United States Patent
Molina

(10) Patent No.: US 11,684,485 B1
(45) Date of Patent: Jun. 27, 2023

(54) SURGICALLY IMPLANTABLE JOINT SPACER

(71) Applicant: Guillermo Molina, Miami, FL (US)

(72) Inventor: Guillermo Molina, Miami, FL (US)

( * ) Notice: Subject to any disclaimer, the term of this patent is extended or adjusted under 35 U.S.C. 154(b) by 218 days.

(21) Appl. No.: 17/168,068

(22) Filed: Feb. 4, 2021

Related U.S. Application Data

(60) Provisional application No. 62/970,160, filed on Feb. 4, 2020.

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2002/3093* (2013.01); *A61F 2002/30143* (2013.01); *A61F 2002/30154* (2013.01); *A61F 2002/30171* (2013.01); *A61F 2002/30301* (2013.01); *A61F 2002/30405* (2013.01); *A61F 2002/30579* (2013.01); *A61F 2002/30624* (2013.01); *A61F 2002/30827* (2013.01); *A61F 2002/30934* (2013.01)

(58) Field of Classification Search
CPC .. A61F 2/447; A61F 2/44; A61F 2/442; A61F 2/30771; A61F 2002/30143; A61F 2002/30154; A61F 2002/30171; A61F 2002/30301; A61F 2002/30405; A61F 2002/30579; A61F 2002/30624; A61F 2002/30827; A61F 2002/3093; A61F 2002/30934
USPC ........................................... 623/17.11–17.16
See application file for complete search history.

(56) References Cited

U.S. PATENT DOCUMENTS

| | | | |
|---|---|---|---|
| 3,986,383 A | * | 10/1976 | Petteys .................. B21D 39/20 D8/51 |
| 5,059,193 A | | 10/1991 | Kuslich |
| 5,116,357 A | | 5/1992 | Eberbach |
| 5,147,374 A | | 9/1992 | Fernandez |
| 5,160,323 A | | 11/1992 | Andrew |
| 5,171,278 A | * | 12/1992 | Pisharodi ................ A61F 2/446 606/279 |

(Continued)

FOREIGN PATENT DOCUMENTS

| EP | 1259179 | 11/2002 |
|---|---|---|
| EP | 1928332 | 6/2008 |

(Continued)

*Primary Examiner* — Jessica Weiss
(74) *Attorney, Agent, or Firm* — Allen D Hertz, P. A.; Allen D. Hertz

(57) ABSTRACT

A surgically implantable spacer including an upper and lower saddle member. Each of a proximal end and a distal end of the saddle members are hingeably assembled to respective upper and lower control arm members. The upper and lower control arm members pivot about a respective proximal and distal pivot member. Spacing between the proximal and distal pivot members is controlled by a control member. The control member is preferably threaded. As the pivot members are drawn together by the control member, the upper and lower saddle members separate from one another. Once one end of each of the upper and lower saddle members contacts the surface of the joint, the other end of each of the upper and lower saddle member can continue to separate until complete contact and sufficient support is provided to the opposing surfaces of the joint.

20 Claims, 21 Drawing Sheets

(56) References Cited

U.S. PATENT DOCUMENTS

| | | | |
|---|---|---|---|
| 5,195,505 | A | 3/1993 | Josefsen |
| 5,199,419 | A | 4/1993 | Remiszewski et al. |
| 5,245,987 | A | 9/1993 | Redmond et al. |
| 5,381,788 | A | 1/1995 | Matula et al. |
| 5,456,695 | A | 10/1995 | Herve Dallemagne |
| 5,514,157 | A | 5/1996 | Nicholas et al. |
| 5,554,101 | A | 9/1996 | Matula et al. |
| 5,662,702 | A | 9/1997 | Keranen |
| 5,665,122 | A * | 9/1997 | Kambin ............... A61F 2/4611 606/279 |
| 5,683,449 | A | 11/1997 | Marcade |
| 5,693,100 | A * | 12/1997 | Pisharodi ............... A61F 2/446 623/17.16 |
| 5,722,935 | A | 3/1998 | Christian |
| 5,755,769 | A | 5/1998 | Richard et al. |
| 5,769,884 | A | 6/1998 | Solovay |
| 5,800,526 | A | 9/1998 | Anderson |
| 5,928,239 | A | 7/1999 | Mirza |
| 5,948,002 | A | 9/1999 | Bonutti |
| 6,039,761 | A * | 3/2000 | Li ............... A61F 2/4455 623/17.16 |
| 6,077,297 | A | 6/2000 | Robinson et al. |
| 6,126,689 | A * | 10/2000 | Brett ............... A61F 2/4455 623/17.15 |
| 6,395,035 | B2 | 5/2002 | Bresina |
| 6,425,887 | B1 | 7/2002 | McGuckin et al. |
| 6,592,559 | B1 | 7/2003 | Pakter et al. |
| 6,595,998 | B2 | 7/2003 | Johnson et al. |
| 6,746,451 | B2 | 6/2004 | Middleton et al. |
| 6,923,813 | B2 | 8/2005 | Phillips et al. |
| 6,939,369 | B2 | 9/2005 | Osborne et al. |
| 7,070,598 | B2 * | 7/2006 | Lim ............... A61F 2/442 623/17.16 |
| 7,166,131 | B2 | 1/2007 | Studer et al. |
| 7,217,293 | B2 * | 5/2007 | Branch, Jr. ........... A61F 2/4611 623/17.11 |
| 7,226,474 | B2 | 6/2007 | Iancea et al. |
| 7,238,186 | B2 | 7/2007 | Zdeblick |
| 7,608,100 | B2 | 10/2009 | Osborne et al. |
| 7,645,301 | B2 | 1/2010 | Hudgins |
| 7,666,226 | B2 | 2/2010 | Schaller |
| 7,758,647 | B2 | 7/2010 | Arnin et al. |
| 7,763,028 | B2 * | 7/2010 | Lim ............... A61B 17/8858 606/90 |
| 7,857,857 | B2 | 12/2010 | Kim |
| 7,955,384 | B2 | 6/2011 | Rafiee |
| 7,959,652 | B2 * | 6/2011 | Zucherman ........ A61B 17/7068 606/279 |
| 8,097,018 | B2 | 1/2012 | Malandain |
| 8,206,291 | B2 | 6/2012 | Fischvogt et al. |
| 8,231,639 | B2 | 7/2012 | Bolduc et al. |
| 8,231,678 | B2 | 7/2012 | Lambrecht |
| 8,236,055 | B2 | 8/2012 | Cordaro |
| 8,439,972 | B2 | 5/2013 | Badawi |
| 8,465,494 | B2 | 6/2013 | Butler et al. |
| 8,470,043 | B2 | 6/2013 | Schaller et al. |
| 8,512,408 | B2 * | 8/2013 | Miller ................ A61F 2/4425 623/17.16 |
| 8,529,628 | B2 | 9/2013 | Marino |
| 8,641,769 | B2 | 2/2014 | Malandain |
| 8,778,027 | B2 | 7/2014 | Medina |
| 9,005,291 | B2 * | 4/2015 | Loebl ................ A61F 2/4611 623/17.15 |
| 9,320,611 | B2 | 4/2016 | Rodriguez |
| 10,258,480 | B1 | 4/2019 | Rodriguez |
| 2003/0176911 | A1 | 9/2003 | Iancea et al. |
| 2003/0191517 | A1 | 10/2003 | Osborne et al. |
| 2004/0117004 | A1 | 6/2004 | Osborne et al. |
| 2004/0186354 | A1 | 9/2004 | LiDonnici |
| 2004/0267269 | A1 | 12/2004 | Middleton et al. |
| 2005/0240193 | A1 | 10/2005 | Layne et al. |
| 2006/0149306 | A1 | 7/2006 | Hart et al. |
| 2006/0282166 | A1 | 12/2006 | Molz et al. |
| 2006/0293753 | A1 | 12/2006 | Thramann |
| 2007/0168041 | A1 | 7/2007 | Kadiyala |
| 2007/0276462 | A1 | 11/2007 | Iancea et al. |
| 2008/0039877 | A1 | 2/2008 | Kammerer |
| 2008/0114364 | A1 | 5/2008 | Goldin et al. |
| 2008/0140084 | A1 | 6/2008 | Osorio et al. |
| 2008/0140203 | A1 | 6/2008 | Davis |
| 2008/0161847 | A1 | 7/2008 | Sandhu et al. |
| 2008/0183044 | A1 | 7/2008 | Colleran et al. |
| 2008/0242940 | A1 | 10/2008 | Stefanchik |
| 2008/0281364 | A1 | 11/2008 | Chirico et al. |
| 2009/0012564 | A1 | 1/2009 | Chirico et al. |
| 2009/0118836 | A1 | 5/2009 | Cordaro |
| 2009/0138043 | A1 | 5/2009 | Kohm |
| 2009/0148591 | A1 | 6/2009 | Wang et al. |
| 2009/0163918 | A1 | 6/2009 | Levy |
| 2009/0204216 | A1 | 8/2009 | Biedermann et al. |
| 2009/0326461 | A1 | 12/2009 | Gresham |
| 2010/0063548 | A1 | 3/2010 | Wang |
| 2010/0076445 | A1 | 3/2010 | Pagano |
| 2010/0130824 | A1 | 5/2010 | Piskun |
| 2010/0174267 | A1 | 7/2010 | McGuckin, Jr. |
| 2010/0185161 | A1 | 7/2010 | Pellegrino et al. |
| 2010/0228289 | A1 | 9/2010 | Park |
| 2011/0004308 | A1 | 1/2011 | Marino et al. |
| 2011/0054260 | A1 | 3/2011 | Albrecht et al. |
| 2011/0054538 | A1 | 3/2011 | Zehavi et al. |
| 2011/0093075 | A1 | 4/2011 | Duplesis et al. |
| 2011/0245926 | A1 | 10/2011 | Kitchen |
| 2012/0116520 | A1 | 5/2012 | Cauthen, III et al. |
| 2013/0123927 | A1 | 5/2013 | Malandain |

FOREIGN PATENT DOCUMENTS

| | | |
|---|---|---|
| WO | WO 2005/097006 | 10/2005 |
| WO | WO 2007/002602 | 1/2007 |
| WO | WO 2007/117908 | 10/2007 |
| WO | WO 2008/022206 | 2/2008 |

\* cited by examiner

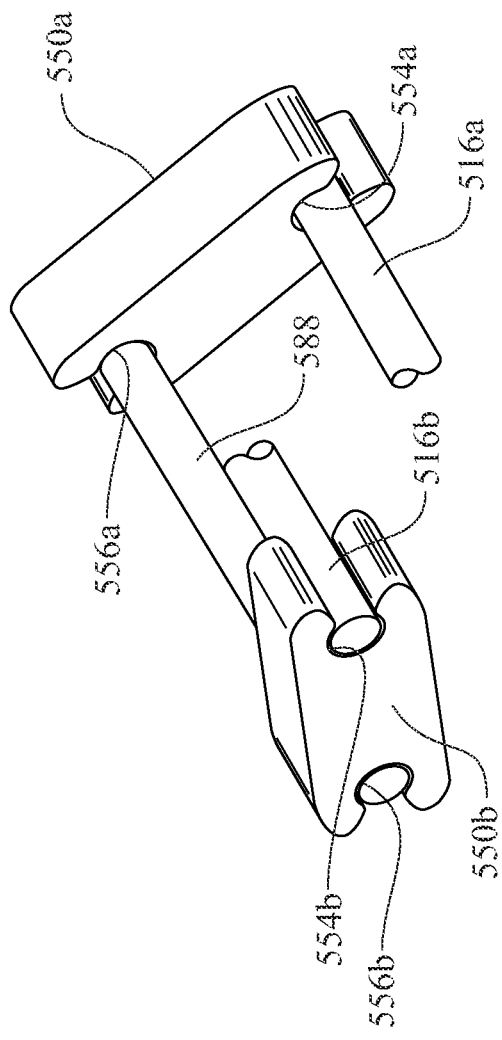
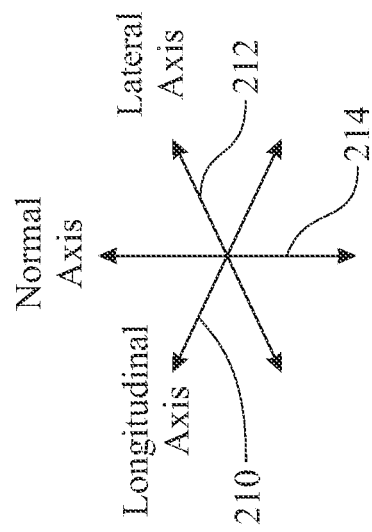
FIG. 19

SURGICALLY IMPLANTABLE JOINT SPACER

FIELD OF THE INVENTION

The present disclosure generally relates to a medically implanted spacer. More particularly, the present disclosure relates to a medically implanted spacer for insertion within a joint formed between two adjacent bones to enhance movement or fuse in a deteriorated biological joint. In one exemplary embodiment, the two adjacent bones are vertebra.

BACKGROUND OF THE INVENTION

Biological joints can degrade over time, deteriorate as a result of a birth defect or a disease, become damaged as a result of an accident or unwarranted motion, malformations due to incorrect growths, and the like. As the joint deviates from a normal, mobile condition, the malformed joint can cause multiple issues to the individual or animal, including sporadic pain or constant pain, limited motion, any degree of incapacitation, and the like.

Common joints that require surgical attention include inter-vertebrae discs, hips, knees, shoulders, elbows, and the like.

Inter-vertebrae discs can degrade over time or become damaged where they no longer function properly. The defective inter-vertebrae discs allow unwarranted motion between two adjacent vertebrae. The defective inter-vertebrae discs limit or reduce the support along the individual's spine. Over time, the defective inter-vertebrae disc needs surgical attention. Inter-vertebrae discs are addressed by fusing two or more adjacent vertebrae together. One short-term drawback of this procedure is the resulting limitation of motion incurred by the individual. A long-term drawback is that over time, the fused region increases stresses on adjacent joints, resulting in additional surgical procedures to fuse other regions of the individual's spine.

Other joints, such as hips and shoulders, are commonly formed having a first end of one bone moveably engaged with a mating end of a mating bone. Most joints comprise a first joint member formed in a ball and the mating joint member formed in a socket. As either or both of the surfaces of the joint members wears or deteriorates, the support of the joint degrades, hindering the mobility of the individual. In addition to the reduced mobility, the deteriorating joint can cause inflammation, discomfort, and other unwanted physical and psychological issues.

The surgically implantable device must meet certain criteria. The surgically implantable device must be expandable. The surgically implantable device must be capable of locking into an expanded configuration. The surgically implantable device to be inserted into a joint while passing through a small opening, then expand into a configuration which provides support across the subject joint. The surgically implantable device must be capable of supporting a joint having differing spans along an elongated length of the surgically implantable device, such as two non-parallel surfaces.

Therefore, what is desired is a device capable of being surgically implanted to repair or overcome medial deficiencies of a damaged or defective biological joint.

SUMMARY OF THE INVENTION

The present disclosure is generally directed to a surgically implanted spacer for use in a joint formed between adjoining ends of two bones.

In a first aspect, the surgically implantable spacer may include:
- a first or lower central disc replacement saddle member;
- a second or upper central disc replacement saddle member;
- a first or lower proximal expansion control arm member;
- a second or upper proximal expansion control arm member;
- a first or lower distal expansion control arm member;
- a second or upper distal expansion control arm member;
- a proximal control arm rotational pivot shaft member;
- a distal control arm rotational pivot shaft member; and
- a threaded control member,
- wherein the first or lower central disc replacement saddle member and the first or lower proximal expansion control arm member are hingeably assembled at a proximal end of the first or lower central disc replacement saddle member,
- wherein the first or lower central disc replacement saddle member and the first or lower distal expansion control arm member are hingeably assembled at a distal end of the first or lower central disc replacement saddle member,
- wherein the second or upper central disc replacement saddle member and the second or upper proximal expansion control arm member are hingeably assembled a proximal end of the second or upper central disc replacement saddle member,
- wherein the second or upper central disc replacement saddle member and the second or upper distal expansion control arm member are hingeably assembled at a distal end of the second or upper central disc replacement saddle member,
- wherein the first or lower proximal expansion control arm member and the second or upper proximal expansion control arm member are hingeably assembled to pivot about a proximal end of the surgically implantable spacer,
- wherein the first or lower distal expansion control arm member and the second or upper distal expansion control arm member are hingeably assembled to pivot about a distal end of the surgically implantable spacer,
- wherein the threaded control member is arranged to draw the proximal end of the surgically implantable spacer and the distal end of the surgically implantable spacer towards one another causing the first or lower central disc replacement saddle member and the second or upper central disc replacement saddle member to separate from one another.

In a second aspect, the threaded control member includes a threaded control member drive head located at a drive end of a shank section.

In another aspect, the threaded control member drive head is formed having a hexagonal shaped exterior surface.

In another aspect, the threaded control member drive head is formed having a square shaped exterior surface.

In another aspect, the threaded control member drive head is formed having a twelve point shaped exterior surface.

In yet another aspect, the shank section of the threaded control member includes a threaded section.

In yet another aspect, the shank section of the threaded control member includes a threaded shank segment and a smooth shank segment, wherein the smooth shank segment is located proximate the drive head.

In another aspect, the threaded control member drive head includes one of a flat or straight drive slot, a crossing or Phillips drive slot, a square bore, a hexagonal bore, a star shaped or TORX® bore, and the like.

In another aspect, the threaded control member drive head includes a flat or straight drive slot, wherein the flat or straight drive slot is configured to receive a standard or flat head screw driver.

In another aspect, the threaded control member drive head includes a crossing or Phillips drive slot, wherein the crossing drive slot is configured to receive a Philips head screw driver.

In another aspect, the threaded control member drive head includes a square bore, wherein the square bore is configured to receive a square driver.

In another aspect, the threaded control member drive head includes a hexagonal bore, wherein the hexagonal bore is configured to receive an Allen head driver.

In another aspect, the threaded control member drive head includes a star shaped or TORX® bore, wherein the tar shaped bore is configured to receive a TORX® head driver.

In yet another aspect, the first or lower proximal expansion control arm member and the second or upper proximal expansion control arm member are hingeably assembled to a proximal control arm rotational pivot shaft member.

In yet another aspect, the first or lower proximal expansion control arm member and the second or upper proximal expansion control arm member are hingeably assembled to at least one pivot shaft of the proximal control arm rotational pivot shaft member.

In yet another aspect, the first or lower distal expansion control arm member and the second or upper distal expansion control arm member are hingeably assembled to a distal control arm rotational pivot shaft member.

In yet another aspect, the first or lower distal expansion control arm member and the second or upper distal expansion control arm member are hingeably assembled to at least one pivot shaft of the distal control arm rotational pivot shaft member.

In yet another aspect, the first or lower central disc replacement saddle member and the first or lower proximal expansion control arm member are hingeably assembled to one another at the proximal end of the first or lower central disc replacement saddle member.

In yet another aspect, the first or lower central disc replacement saddle member and the first or lower distal expansion control arm member are hingeably assembled to one another at the distal end of the first or lower central disc replacement saddle member.

In yet another aspect, the second or upper central disc replacement saddle member and the second or upper proximal expansion control arm member are hingeably assembled to one another at the proximal end of the second or upper central disc replacement saddle member.

In yet another aspect, the second or upper central disc replacement saddle member and the second or upper distal expansion control arm member are hingeably assembled to one another at the distal end of the second or upper central disc replacement saddle member.

In yet another aspect, at least one hinge assembly comprises a first hinge formation and a second hinge formation, wherein the first hinge formation and the second hinge formation enable rotation therebetween when assembled to one another.

In yet another aspect, at least one hinge assembly comprises a first hinge formation and a second hinge formation, wherein the first hinge formation and the second hinge formation enable rotation therebetween when assembled to one another, wherein the first hinge formation is provided having an interior surface formed in a semi-circular shape and the second hinge formation has an exterior surface that formed having one of a semi-circular or circular shape.

In yet another aspect, each hinge assembly comprises the first hinge formation and the second hinge formation, wherein the first hinge formation and the second hinge formation enable rotation therebetween when assembled to one another, wherein the first hinge formation is provided having an interior surface formed in a semi-circular shape and the second hinge formation has an exterior surface that formed having one of a semi-circular or circular shape.

In yet another aspect, the rotation of the hinge assemblies is about a lateral axis.

In yet another aspect, at least one of the first hinge formation and the second hinge formation comprises a gap.

In yet another aspect, at least one of the first hinge formation and the second hinge formation comprises a gap extending inward along a longitudinal direction.

In yet another aspect, at least one of the first hinge formation and the second hinge formation of at least one hinge assembly comprises a gap extending inward along a longitudinal direction.

In yet another aspect, at least one of the first hinge formation and the second hinge formation of each hinge assembly comprises a gap extending inward along a longitudinal direction.

In yet another aspect, each of the first hinge formation and the second hinge formation comprises a gap.

In yet another aspect, each of the first hinge formation and the second hinge formation comprises a gap extending inward along a longitudinal direction.

In yet another aspect, each of the first hinge formation and the second hinge formation of at least one hinge assembly comprises a gap extending inward along a longitudinal direction.

In yet another aspect, each of the first hinge formation and the second hinge formation of each hinge assembly comprises a gap extending inward along a longitudinal direction.

In yet another aspect, at least a portion of the first hinge formation is inserted into a gap formed in the second hinge formation of at least one hinge assembly comprises a gap extending inward along a longitudinal direction.

In yet another aspect, at least a portion of the second hinge formation is inserted into a gap formed in the first hinge formation of at least one hinge assembly comprises a gap extending inward along a longitudinal direction.

In yet another aspect, at least a portion of the first hinge formation is inserted into a gap formed in the second hinge formation of each hinge assembly comprises a gap extending inward along a longitudinal direction.

In yet another aspect, at least a portion of the second hinge formation is inserted into a gap formed in the first hinge formation of each hinge assembly comprises a gap extending inward along a longitudinal direction.

In yet another aspect, the first or lower proximal expansion control arm member and the second or upper proximal expansion control arm member are hingeably assembled to at least one pivot shaft of the proximal control arm rotational pivot shaft member, wherein the hinge formation is provided having an interior surface formed in a semi-circular shape and of a size and shape to snap onto the mating hinge element.

In yet another aspect, the first or lower proximal expansion control arm member and the second or upper proximal expansion control arm member are hingeably assembled to at least one pivot shaft of the proximal control arm rotational pivot shaft member, wherein the hinge formation is provided having an interior surface formed in a semi-circular shape and of a size and shape to snap onto the respective pivot shaft of the at least one pivot shaft.

In yet another aspect, the first or lower distal expansion control arm member and the second or upper distal expansion control arm member are hingeably assembled to at least one pivot shaft of the distal control arm rotational pivot shaft member, wherein the hinge formation is provided having an interior surface formed in a semi-circular shape and of a size and shape to snap onto the mating hinge element.

In yet another aspect, the first or lower distal expansion control arm member and the second or upper distal expansion control arm member are hingeably assembled to at least one pivot shaft of the distal control arm rotational pivot shaft member, wherein the hinge formation is provided having an interior surface formed in a semi-circular shape and of a size and shape to snap onto the respective pivot shaft of the at least one pivot shaft.

In yet another aspect, the semi-circular shape of the hinge formation can be provided as an enclosed circular shape, wherein an interior surface of the enclosed circular shape is a size and shape to slideably assembly onto the mating hinge element.

In yet another aspect, the semi-circular shape of the hinge formation can be provided as an enclosed circular shape, wherein an interior surface of the enclosed circular shape is a size and shape to slideably assembly onto the respective pivot shaft of the at least one pivot shaft.

In yet another aspect, the first or lower proximal expansion control arm member comprises a first hinge formation provided proximate a laterally first edge and a second hinge formation provided proximate a laterally second edge.

In yet another aspect, the first or lower proximal expansion control arm member comprises a first hinge formation provided proximate a laterally first edge and a second hinge formation provided proximate a laterally second edge providing a gap therebetween, wherein the gap straddles a segment of the threaded control member.

In yet another aspect, the second or upper proximal expansion control arm member comprises a first hinge formation provided proximate a laterally first edge and a second hinge formation provided proximate a laterally second edge.

In yet another aspect, the second or upper proximal expansion control arm member comprises a first hinge formation provided proximate a laterally first edge and a second hinge formation provided proximate a laterally second edge providing a gap therebetween, wherein the gap straddles a segment of the threaded control member.

In yet another aspect, the first or lower proximal expansion control arm member comprises a first or lower proximal expansion control arm bridge segment extending between the first hinge formation and the second hinge formation.

In yet another aspect, the second or upper proximal expansion control arm member comprises a second or upper proximal expansion control arm bridge segment extending between the first hinge formation and the second hinge formation.

In yet another aspect, the bridge segment of each proximal expansion control arm member further comprising a contraction element clearance, wherein the contraction element clearance is of a size and shape to avoid interference with elements of the threaded control member.

In yet another aspect, the first or lower distal expansion control arm member comprises a first or lower distal expansion control arm bridge segment extending between the first hinge formation and the second hinge formation.

In yet another aspect, the second or upper distal expansion control arm member comprises a second or upper distal expansion control arm bridge segment extending between the first hinge formation and the second hinge formation.

In yet another aspect, the first or lower proximal expansion control arm member further comprising a first or lower distal expansion control arm transverse assembly retention element, wherein the first or lower distal expansion control arm transverse assembly retention element is located proximate the first or lower distal expansion control arm first central hinge connecting formation to retain a lateral position of the first or lower central disc replacement saddle member.

In yet another aspect, the bridge segment of each distal expansion control arm member further comprising a contraction element clearance, wherein the contraction element clearance is of a size and shape to avoid interference with elements of the distal control arm rotational pivot shaft member.

In yet another aspect, the proximal control arm rotational pivot shaft member further comprising a smooth walled bore extending longitudinally and terminating at a flange, wherein the smooth walled bore has a diameter that is proximate a diameter of an engaging section of the threaded control member.

In yet another aspect, the proximal control arm rotational pivot shaft member further comprising a smooth walled bore extending longitudinally and terminating at a flange, wherein the smooth walled bore has a diameter that is proximate a diameter of an engaging section of the threaded control member, the smooth walled bore having a diameter that is larger than a maximum diameter of a drive head of the threaded control member and wherein an opening of the flange is smaller than the diameter of the drive head of the threaded control member.

In yet another aspect, the proximal control arm rotational pivot shaft member further comprising a smooth walled bore extending longitudinally and terminating at a flange, wherein the smooth walled bore has a diameter that is proximate a diameter of an engaging section of the threaded control member, the smooth walled bore having a diameter that is larger than a maximum diameter of a drive head of the threaded control member, wherein a depth of the smooth walled bore is proximate or greater than an elongated dimension of the drive head of the threaded control member, wherein an opening of the flange is smaller than the diameter of the drive head of the threaded control member.

In yet another aspect, the proximal control arm rotational pivot shaft member further comprising a smooth walled bore extending longitudinally and terminating at a flange, wherein the smooth walled bore has a diameter that is proximate a diameter of an engaging section of the threaded control member, the smooth walled bore having a diameter that is larger than a maximum diameter of a drive head of the threaded control member, wherein a depth of the smooth walled bore is slightly less than an elongated dimension of the drive head of the threaded control member, wherein an opening of the flange is smaller than the diameter of the drive head of the threaded control member. The term slightly less than can be defined where a small percentage of the drive head is slightly exposed form the smooth wall bore.

In yet another aspect, the diameter of the smooth walled bore is of a size enabling insertion of a drive tool between the smooth walled bore and the drive head of the threaded control member.

In yet another aspect, the proximal control arm rotational pivot shaft member further comprising a pair of proximal control arm rotational pivot shafts, each proximal control arm rotational pivot shaft extending laterally outward from a respective side of a proximal control arm proximal end block.

In yet another aspect, the proximal control arm rotational pivot shaft member further comprising the pair of proximal control arm rotational pivot shafts, each proximal control arm rotational pivot shaft extending laterally outward from a respective side of the proximal control arm proximal end block, the proximal control arm proximal end block further comprising a smooth walled bore extending longitudinally and terminating at the flange, wherein the smooth walled bore has a diameter that is proximate the diameter of the engaging section of the threaded control member.

In yet another aspect, the distal control arm rotational pivot shaft member further comprising a threaded bore extending longitudinally inward from a proximal end thereof, wherein the threaded bore has a thread pitch and diameter that is configured to threadably engage with a threaded section of the threaded control member, the threaded section having the same thread pitch and diameter as the threaded bore.

In yet another aspect, the distal control arm rotational pivot shaft member further comprising a pair of distal control arm rotational pivot shafts, each distal control arm rotational pivot shaft extending laterally outward from a respective side of a distal control arm proximal end block.

In yet another aspect, the distal control arm rotational pivot shaft member further comprising the pair of distal control arm rotational pivot shafts, each distal control arm rotational pivot shaft extending laterally outward from a respective side of the distal control arm proximal end block, the distal control arm distal end block further comprising a threaded bore extending longitudinally inward from a proximal end thereof, wherein the threaded bore has a thread pitch and diameter that is configured to threadably engage with a threaded section of the threaded control member, the threaded section having the same thread pitch and diameter as the threaded bore.

In yet another aspect, the distal control arm rotational pivot shaft member further comprising the pair of distal control arm rotational pivot shafts, each distal control arm rotational pivot shaft extending laterally outward from a respective side of the distal control arm proximal end block, the distal control arm distal end block further comprising a threaded bore extending longitudinally inward from a proximal end thereof, wherein the threaded bore has a thread pitch and diameter that is configured to threadably engage with a threaded section of the threaded control member, the threaded section having the same thread pitch and diameter as the threaded bore, wherein the threaded bore has a depth that enables maximum contraction between the proximal end of the surgically implantable spacer and the distal end of the surgically implantable spacer.

In yet another aspect, the distal control arm rotational pivot shaft member further comprising a threaded member receiving block, wherein the threaded member receiving block is connected to the distal control arm distal end block.

In yet another aspect, the distal control arm rotational pivot shaft member further comprising a threaded member receiving block, wherein the threaded member receiving block is connected to the distal control arm distal end block by a distal control arm connecting shaft.

In yet another aspect, the surgically implantable spacer further comprising at least one feature for assistance during installation of the surgically implantable spacer into a joint of a patient. One exemplary application of the surgically implantable spacer is a replacement for an inter-vertebrae disc.

In yet another aspect, a vertebral contacting surface of the first or lower central disc replacement saddle member has an arched shape.

In yet another aspect, a vertebral contacting surface of the first or lower central disc replacement saddle member has an outwardly extending, arched shape.

In yet another aspect, a vertebral contacting surface of the second or upper central disc replacement saddle member has an arched shape.

In yet another aspect, a vertebral contacting surface of the second or upper central disc replacement saddle member has an outwardly extending, arched shape.

In yet another aspect, a vertebral contacting surface of the first or lower central disc replacement saddle member is textured.

In yet another aspect, a vertebral contacting surface of the first or lower central disc replacement saddle member is textured to improve positioning retention between the surgically implantable spacer and the adjacent vertebrae.

In yet another aspect, the texture of the vertebral contacting surface of the first or lower central disc replacement saddle member is scalloped.

In yet another aspect, the texture of the vertebral contacting surface of the first or lower central disc replacement saddle member comprises a series of recesses and ridges.

In yet another aspect, the texture of the vertebral contacting surface of the first or lower central disc replacement saddle member comprises a series of alternating recesses and ridges.

In yet another aspect, the texture of the vertebral contacting surface of the first or lower central disc replacement saddle member comprises a series of alternating recesses and ridges having a parallel arrangement.

In yet another aspect, the texture of the vertebral contacting surface of the first or lower central disc replacement saddle member comprises a series of alternating recesses and ridges having a laterally oriented arrangement.

In yet another aspect, the texture of the vertebral contacting surface of the first or lower central disc replacement saddle member comprises a series of alternating recesses and ridges having a parallel, laterally oriented arrangement.

In yet another aspect, the texture of the vertebral contacting surface of the first or lower central disc replacement saddle member comprises a series of cross hatched formations, wherein the alternating recesses and ridges are arranged in both a first direction and a second direction.

In yet another aspect, the texture of the vertebral contacting surface of the first or lower central disc replacement saddle member comprises a series of cross hatched formations defined by a series of ridges, wherein the series of ridges are arranged in both a first direction and a second direction, the first direction being parallel to a first angle respective to the elongated axis and the second direction being parallel to a second angle respective to the elongated axis, the first angle and the second angle being different from one another.

In yet another aspect, the texture of the vertebral contacting surface of the first or lower central disc replacement saddle member comprises a series of cross hatched formations defined by a series of ridges, wherein the series of ridges are arranged in both a first direction and a second direction, the first direction being parallel to a first angle respective to the elongated axis and the second direction being parallel to a second angle respective to the elongated axis, the first angle and the second angle being perpendicular to one another.

In yet another aspect, the texture of the vertebral contacting surface of the first or lower central disc replacement saddle member comprises a series of cross hatched formations, wherein the alternating recesses and ridges are arranged in both a first direction and a second direction, the first direction being parallel to a first angle respective to the elongated axis and the second direction being parallel to a second angle respective to the elongated axis, the first angle and the second angle being different from one another.

In yet another aspect, the texture of the vertebral contacting surface of the first or lower central disc replacement saddle member comprises a series of cross hatched formations, wherein the alternating recesses and ridges are arranged in both a first direction and a second direction, the first direction being parallel to a first angle respective to the elongated axis and the second direction being parallel to a second angle respective to the elongated axis, the first angle and the second angle being perpendicular to one another.

In yet another aspect, a vertebral contacting surface of the second or upper central disc replacement saddle member is textured.

In yet another aspect, a vertebral contacting surface of the second or upper central disc replacement saddle member is textured to improve positioning retention between the surgically implantable spacer and the adjacent vertebrae.

In yet another aspect, the texture of the vertebral contacting surface of the second or upper central disc replacement saddle member is scalloped.

In yet another aspect, the texture of the vertebral contacting surface of the second or upper central disc replacement saddle member comprises a series of recesses and ridges.

In yet another aspect, the texture of the vertebral contacting surface of the second or upper central disc replacement saddle member comprises a series of alternating recesses and ridges.

In yet another aspect, the texture of the vertebral contacting surface of the second or upper central disc replacement saddle member comprises a series of alternating recesses and ridges having a parallel arrangement.

In yet another aspect, the texture of the vertebral contacting surface of the second or upper central disc replacement saddle member comprises a series of alternating recesses and ridges having a laterally oriented arrangement.

In yet another aspect, the texture of the vertebral contacting surface of the second or upper central disc replacement saddle member comprises a series of alternating recesses and ridges having a parallel, laterally oriented arrangement.

In yet another aspect, the texture of the vertebral contacting surface of the second or upper central disc replacement saddle member comprises a series of cross hatched formations, wherein the alternating recesses and ridges are arranged in both a first direction and a second direction.

In yet another aspect, the texture of the vertebral contacting surface of the second or upper central disc replacement saddle member comprises a series of cross hatched formations defined by a series of ridges, wherein the series of ridges are arranged in both a first direction and a second direction, the first direction being parallel to a first angle respective to the elongated axis and the second direction being parallel to a second angle respective to the elongated axis, the first angle and the second angle being different from one another.

In yet another aspect, the texture of the vertebral contacting surface of the second or upper central disc replacement saddle member comprises a series of cross hatched formations defined by a series of ridges, wherein the series of ridges are arranged in both a first direction and a second direction, the first direction being parallel to a first angle respective to the elongated axis and the second direction being parallel to a second angle respective to the elongated axis, the first angle and the second angle being perpendicular to one another.

In yet another aspect, the texture of the vertebral contacting surface of the second or upper central disc replacement saddle member comprises a series of cross hatched formations, wherein the alternating recesses and ridges are arranged in both a first direction and a second direction, the first direction being parallel to a first angle respective to the elongated axis and the second direction being parallel to a second angle respective to the elongated axis, the first angle and the second angle being different from one another.

In yet another aspect, the texture of the vertebral contacting surface of the second or upper central disc replacement saddle member comprises a series of cross hatched formations, wherein the alternating recesses and ridges are arranged in both a first direction and a second direction, the first direction being parallel to a first angle respective to the elongated axis and the second direction being parallel to a second angle respective to the elongated axis, the first angle and the second angle being perpendicular to one another.

In yet another aspect, the texture of the vertebral contacting surface of the first or lower central disc replacement saddle member and the texture of the vertebral contacting surface of the second or upper central disc replacement saddle member are the same.

In yet another aspect, the texture of the vertebral contacting surface of the first or lower central disc replacement saddle member and the texture of the vertebral contacting surface of the second or upper central disc replacement saddle member are the different from one another.

In yet another aspect, the first or lower central disc replacement saddle member further comprising a first or lower central disc replacement saddle body central clearance passing vertically therethrough at a central location.

In yet another aspect, the second or upper central disc replacement saddle member further comprising a second or upper central disc replacement saddle body central clearance passing vertically therethrough at a central location.

In yet another aspect, the first or lower central disc replacement saddle body central clearance and the second or upper central disc replacement saddle body central clearance are of a same size.

In yet another aspect, the first or lower central disc replacement saddle body central clearance and the second or upper central disc replacement saddle body central clearance are of a same shape.

In yet another aspect, the first or lower central disc replacement saddle body central clearance and the second or upper central disc replacement saddle body central clearance are of a same size and shape.

In yet another aspect, the first or lower central disc replacement saddle body central clearance and the second or upper central disc replacement saddle body central clearance are of a different size.

In yet another aspect, the first or lower central disc replacement saddle body central clearance and the second or upper central disc replacement saddle body central clearance are of a different shape.

In yet another aspect, the first or lower central disc replacement saddle body central clearance and the second or upper central disc replacement saddle body central clearance are of a different size and shape.

In yet another aspect, the first or lower central disc replacement saddle member further comprising a first or lower central disc replacement saddle contraction element clearance recessed into an interior surface thereof.

In yet another aspect, the second or upper central disc replacement saddle member further comprising a second or upper central disc replacement saddle contraction element clearance recessed into an interior surface thereof.

In yet another aspect, an elongated length of the first or lower proximal expansion control arm member is equal to an elongated length of the second or upper proximal expansion control arm member.

In yet another aspect, an elongated length of the first or lower proximal expansion control arm member is substantially equal to an elongated length of the second or upper proximal expansion control arm member.

In yet another aspect, an elongated length of the first or lower distal expansion control arm member is equal to an elongated length of the second or upper distal expansion control arm member.

In yet another aspect, an elongated length of the first or lower distal expansion control arm member is substantially equal to an elongated length of the second or upper distal expansion control arm member.

In yet another aspect, an elongated length of the first or lower proximal expansion control arm member is shorter than an elongated length of the first or lower distal expansion control arm member.

In yet another aspect, an elongated length of the second or upper proximal expansion control arm member is shorter than an elongated length of the second or upper distal expansion control arm member.

In a first variation, a surgically implantable spacer may include:
- a proximal control arm rotational pivot shaft member comprising a proximal control arm proximal end block, a pair of proximal control arm rotational pivot shafts, each proximal control arm rotational pivot shaft extending linearly outward from opposite sides of the proximal control arm proximal end block, a proximal control arm smooth walled bore extending through the proximal control arm proximal end block in a direction generally perpendicular to an axial direction of the pair of proximal control arm rotational pivot shafts;
- a distal control arm rotational pivot shaft assembly comprising a distal control arm rotational pivot shaft assembled to a threaded member receiving block by an assembly component, a threaded bore extending through the threaded member receiving block in a direction generally perpendicular to an elongated axis of the distal control arm rotational pivot shaft;
- a threaded control member extending through the proximal control arm smooth walled bore and threadably assembled to the threaded bore extending through the threaded member receiving block;
- a first or lower disc replacement support truss assembly comprising a near or first side lower disc replacement support truss, a far or second side lower disc replacement support truss and a first or lower spanning control cross member spanning between distal ends of the near or first side lower disc replacement support truss and the far or second side lower disc replacement support truss, each of the near or first side lower disc replacement support truss and the far or second side lower disc replacement support truss being pivotally assembled to the respective proximal control arm rotational pivot shaft of the pair of proximal control arm rotational pivot shafts;
- a second or upper disc replacement support truss assembly comprising a near or first side upper disc replacement support truss, a far or second side upper disc replacement support truss and a second or upper spanning control cross member spanning between distal ends of the near or first side upper disc replacement support truss and the far or second side upper disc replacement support truss, each of the near or first side upper disc replacement support truss and the far or second side upper disc replacement support truss being pivotally assembled to the respective proximal control arm rotational pivot shaft of the pair of proximal control arm rotational pivot shafts;
- a first or lower truss expansion control member having a first end pivotally assembled to the distal control arm rotational pivot shaft and a second, opposite end pivotally assembled to the first or lower disc replacement support truss spanning control cross member; and
- a second or upper truss expansion control member having a first end pivotally assembled to the distal control arm rotational pivot shaft and a second, opposite end pivotally assembled to the second or upper disc replacement support truss spanning control cross member.

In yet another aspect, the first or lower disc replacement support truss and the second or upper disc replacement support truss replicate one another in shape and size.

In yet another aspect, the first or lower truss expansion control member and the second or upper truss expansion control member replicate one another in shape and size.

In yet another aspect, the threaded control member includes a threaded section and a smooth shank section.

In yet another aspect, the present invention discloses a method of use, the method comprising steps of:
- obtaining a surgically implantable spacer, the surgically implantable spacer being described above;
- expanding a span or distance between a proximal end of the surgically implantable spacer and a distal end of the surgically implantable spacer, minimizing a distance between a lower contacting surface of the surgically implantable spacer and an upper contacting surface of the surgically implantable spacer;
- inserting the surgically implantable spacer into a biological joint;
- contracting a distance between the proximal end of the surgically implantable spacer and the distal end of the surgically implantable spacer, increasing the distance between the lower contacting surface of the surgically implantable spacer and the upper contacting surface of the surgically implantable spacer,
  - wherein the lower contacting surface of the surgically implantable spacer and the upper contacting surface of the surgically implantable spacer move outward from one another in a parallel motion until a first end of the lower contacting surface of the surgically implantable spacer and a same first end of the upper contacting surface of the surgically implantable spacer reaches a condition of substantial resistance in separating bones of the biological joint,
  - wherein, upon reaching a condition of a substantially increased resistance in separation of the biological joint, the first end of the lower contacting surface of the surgically implantable spacer and the same first end of the upper contacting surface of the surgically implantable spacer separate at a slower or reduced rate and a second, opposite end of the lower contacting surface of the surgically implantable spacer and a same second, opposite end of the upper contacting surface of the surgically implantable spacer continue to separate from one another until the second, opposite end of the lower contacting surface of the surgically implantable spacer and the same second, opposite end of the upper contacting surface of the surgically implantable spacer are subjected to a substantially increased resistance in separation of the biological joint.

In yet another aspect, substantially increased resistance refers to a resistance that is greater than a resistance at the second, opposite end of the central member.

In yet another aspect, upon reaching a condition of substantial resistance, the first end of the lower contacting surface of the surgically implantable spacer and the same first end of the upper contacting surface of the surgically implantable spacer remain at a fixed dimension.

In yet another aspect, the method further comprises a step of rotating a threaded control member to contract the span or distance between a proximal end of the surgically implantable spacer and a distal end of the surgically implantable spacer.

In yet another aspect, the method further comprises a step of rotating a threaded control member to contract the span or distance between a proximal end of the surgically implantable spacer and a distal end of the surgically implantable spacer, wherein a distal end of the threaded control member threadably engages with a distal control arm rotational pivot shaft member.

In yet another aspect, the method further comprises a step of rotating a threaded control member to contract the span or distance between a proximal end of the surgically implantable spacer and a distal end of the surgically implantable spacer, wherein a distal end of the threaded control member threadably engages with a threaded member receiving block of the distal control arm rotational pivot shaft member.

In yet another aspect, the method further comprises a step of rotating a threaded control member to contract the span or distance between a proximal end of the surgically implantable spacer and a distal end of the surgically implantable spacer, wherein a distal end of the threaded control member threadably engages with a threaded bore formed within a threaded member receiving block of the distal control arm rotational pivot shaft member.

In yet another aspect, the method further comprises a step of inserting bone graft material between a first or lower central disc replacement saddle member of the surgically implantable spacer and a second or upper central disc replacement saddle member of the surgically implantable spacer.

In yet another aspect, the method further comprises a step of employing at least one transverse assembly retention element to retain the elements of the surgically implantable spacer in a transverse position.

In yet another aspect, the method further comprises a step of interlacing hinge features of different elements.

In yet another aspect, the method further comprises a step of interlacing a hinge feature of a first element with a hinge element of a second element.

In yet another aspect, the method further comprises a step of recessing a drive head of a threaded control member within a proximal control arm rotational pivot shaft member.

In yet another aspect, the method further comprises a step of recessing a drive head of a threaded control member within a proximal control arm proximal end block of the proximal control arm rotational pivot shaft member.

These and other aspects, features, and advantages of the present invention will become more readily apparent from the attached drawings and the detailed description of the preferred embodiments, which follow.

BRIEF DESCRIPTION OF THE DRAWINGS

The invention will now be described, by way of example, with reference to the accompanying drawings, in which:

1, the surgically implantable spacer being shown installed between two adjacent vertebrae, replacing an intra-vertebral disc.

FIG. 19 presents an isometric top, side view of a pair of truss expansion control members of the simplified exemplary surgically implantable spacer originally introduced in FIG. 16, wherein the pair of truss expansion control members provide expansion and contraction between ends of the disc replacement support trusses resulting from a rotational motion of a threaded control member of the expansion and contraction drive portion detailed in FIG. 18;

Like reference numerals refer to like parts throughout the several views of the drawings.

DETAILED DESCRIPTION OF THE INVENTION

Figure 1:
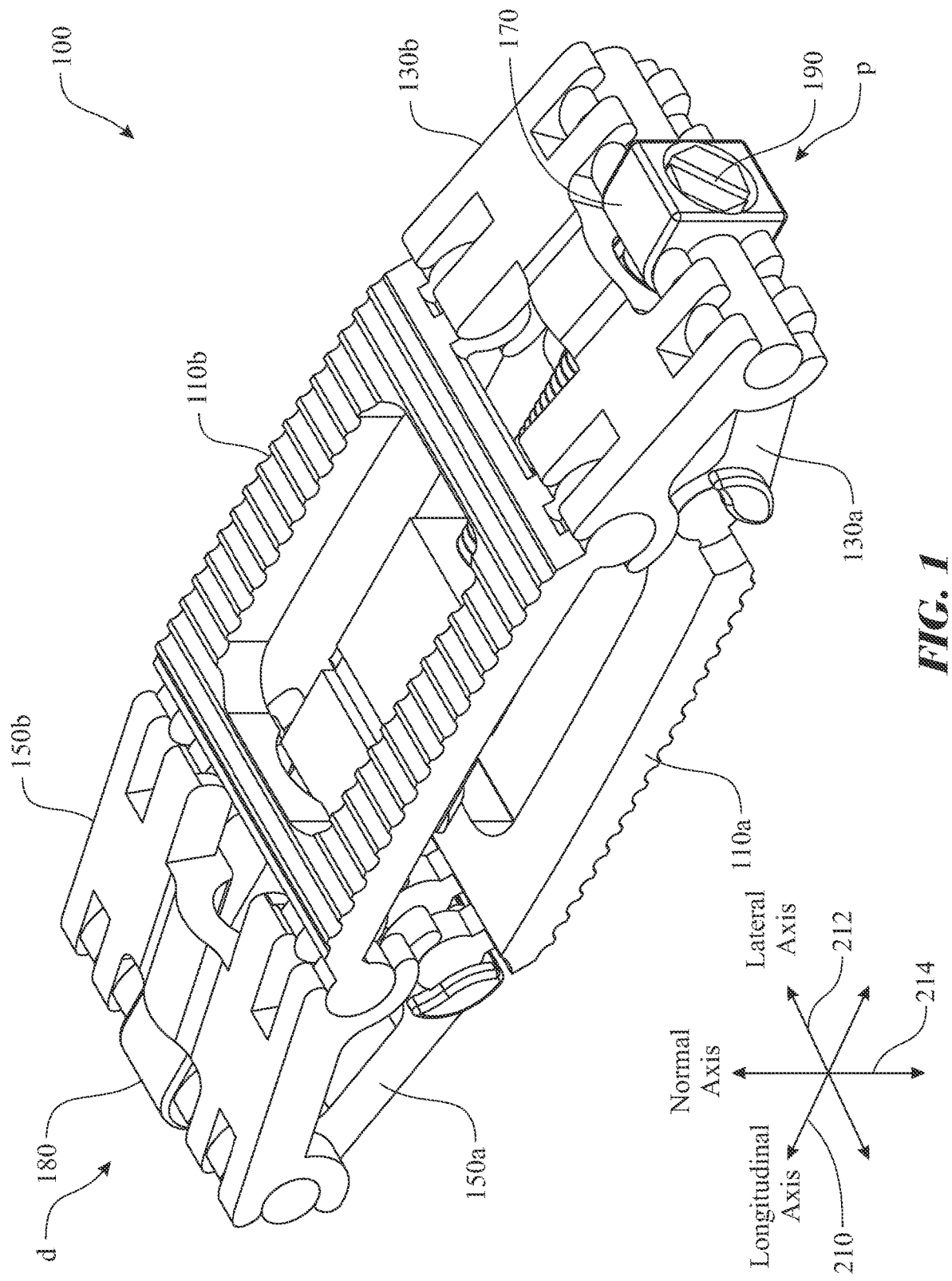
FIG. 1 presents an isometric top, side view of an exemplary surgically implantable spacer taken from a proximal end, the surgically implantable spacer being shown in an insertion configuration.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention is generally directed towards a surgically implantable spacer 100, as illustrated in FIGS. 1 through 12. Orientation of the surgically implantable spacer 100 is referenced by a longitudinal or elongated axis 210, a lateral axis 212, and a normal axis 214.

The surgically implantable spacer 100 includes nine (9) components: a lower central disc replacement saddle member 110a, a upper central disc replacement saddle member 110b, a lower proximal expansion control arm member 130a, a upper proximal expansion control arm member 130b, a lower distal expansion control arm member 150a, a upper distal expansion control arm member 150b, a proximal control arm rotational pivot shaft member 170, a distal control arm rotational pivot shaft member 180, and a threaded control member 190. Orientation of the surgically implantable spacer 100 and the components thereof can be referenced by a proximal end p and a distal end d. A proximal end of the lower central disc replacement saddle member 110a is pivotally assembled to a distal end of the lower proximal expansion control arm member 130a. A distal end of the lower central disc replacement saddle member 110a is pivotally assembled to a proximal end of the lower distal expansion control arm member 150a. A proximal end of the upper central disc replacement saddle member 110b is pivotally assembled to a distal end of the upper proximal expansion control arm member 130b. A distal end of the upper central disc replacement saddle member 110b is pivotally assembled to a proximal end of the upper distal expansion control arm member 150b. A proximal end of the lower proximal expansion control arm member 130a and a proximal end of the upper proximal expansion control arm member 130b pivot about a common lateral pivot axis. The common lateral pivot axis for the lower proximal expansion control arm member 130a and the upper proximal expansion control arm member 130b can be provided by the proximal control arm rotational pivot shaft member 170. A distal end of the lower distal expansion control arm member 150a and a distal end of the upper distal expansion control arm member 150b pivot about a common lateral pivot axis. The common lateral pivot axis for the lower distal expansion control arm member 150a and the upper distal expansion control arm member 150b can be provided by the distal control arm rotational pivot shaft member 180.

Figure 4:
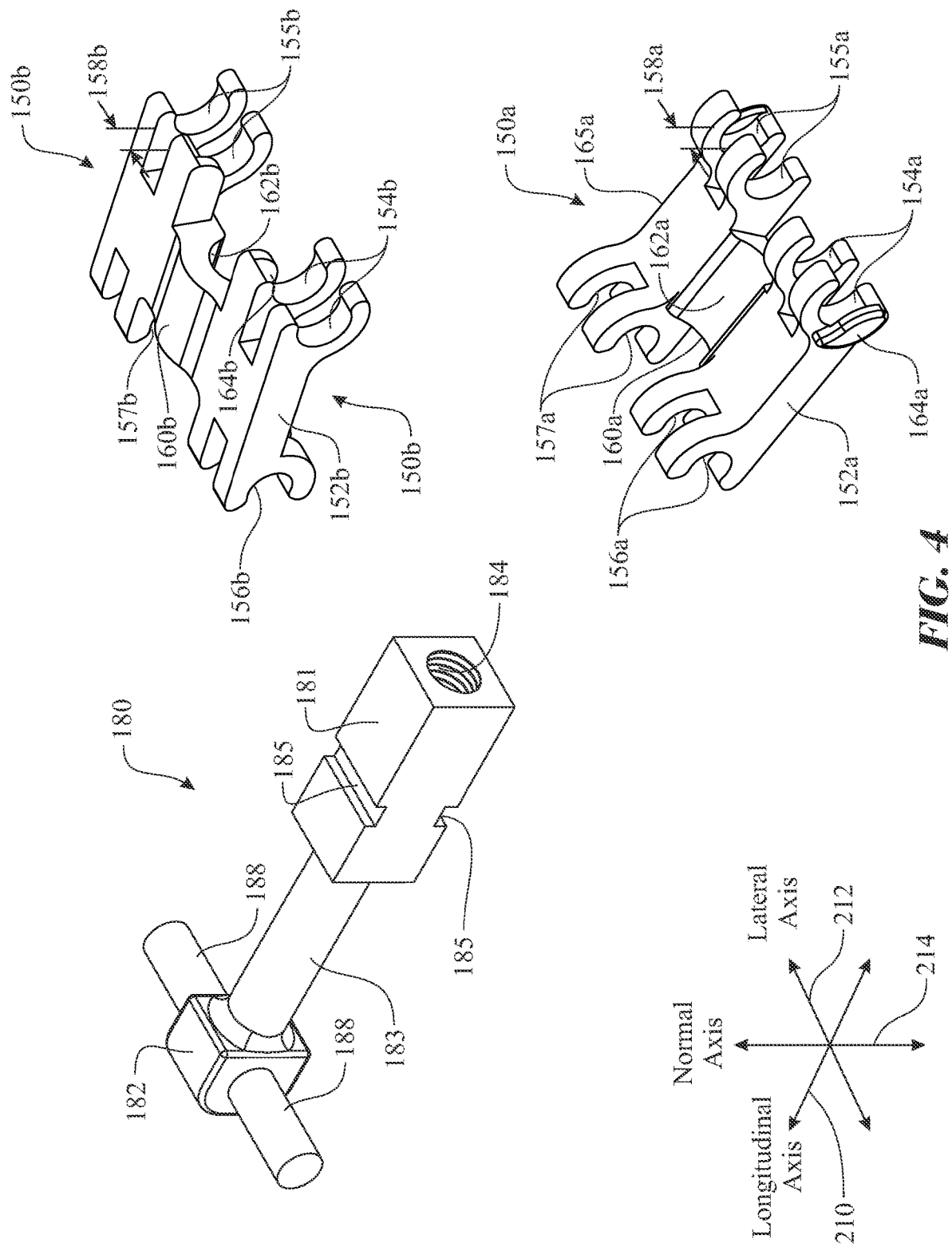
FIG. 4 presents an isometric top, side exploded assembly view of a distal portion of the surgically implantable spacer, originally introduced in FIG. 1, the elements of the distal portion of surgically implantable spacer being shown in a disassembled or preassembly configuration.
Figure 5:
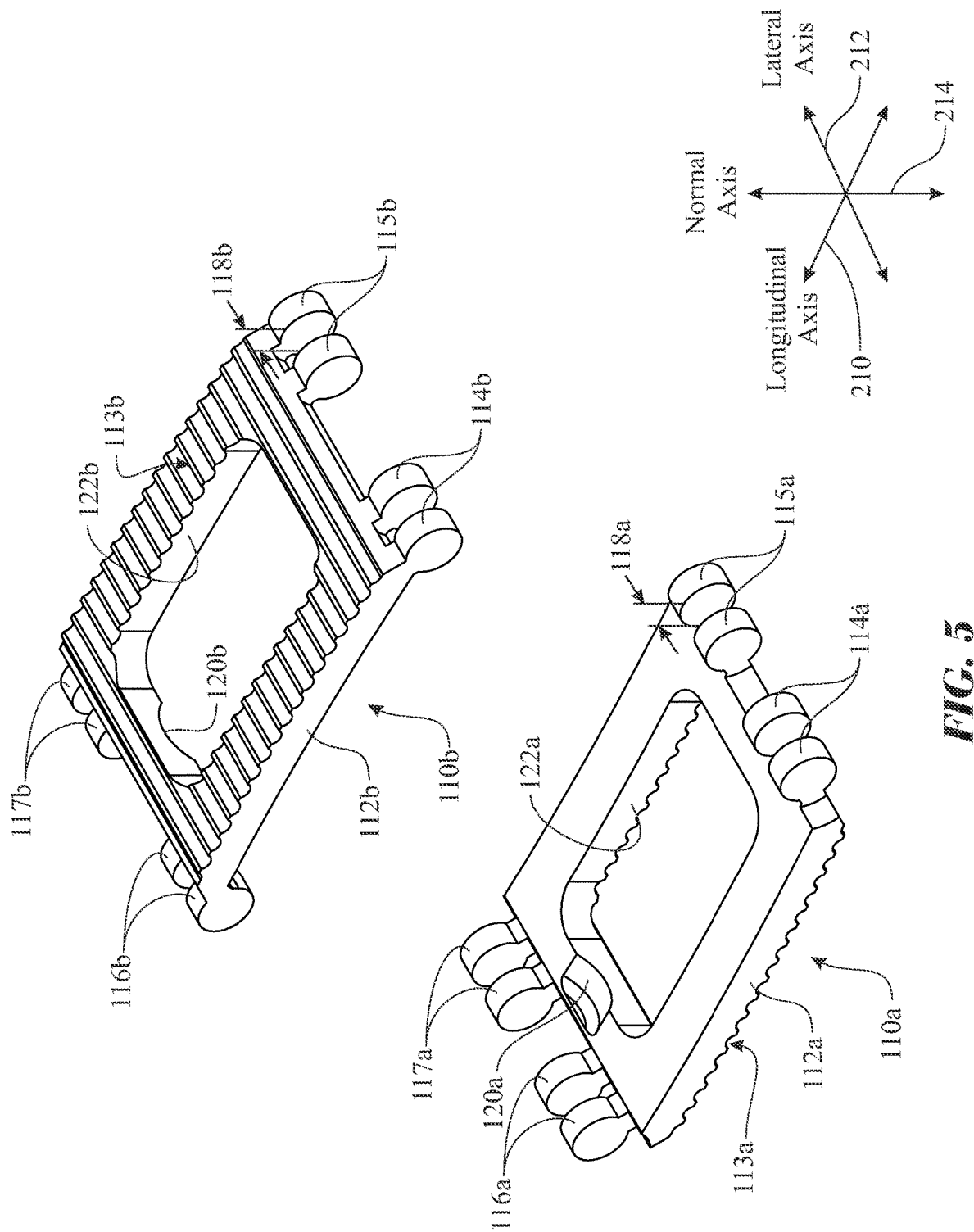
FIG. 5 presents an isometric top, side exploded assembly view of a central portion of the surgically implantable spacer, originally introduced in FIG. 1, the elements of the central portion of surgically implantable spacer being shown in a disassembled or preassembly configuration.
Figure 6:
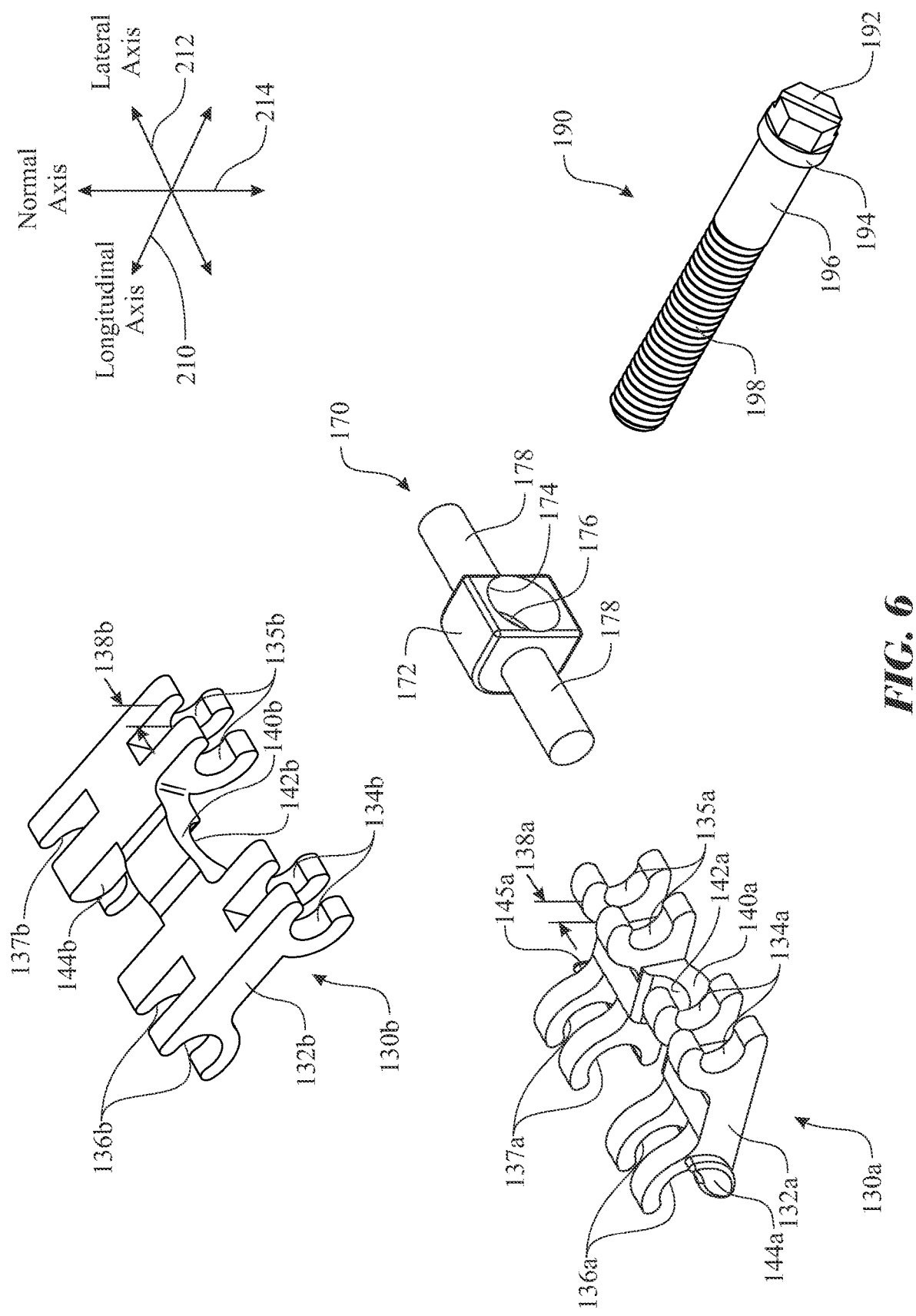
FIG. 6 presents an isometric top, side exploded assembly view of a proximal portion of the surgically implantable spacer, originally introduced in FIG. 1, the elements of the proximal portion of surgically implantable spacer being shown in a disassembled or preassembly configuration.
Figure 7:
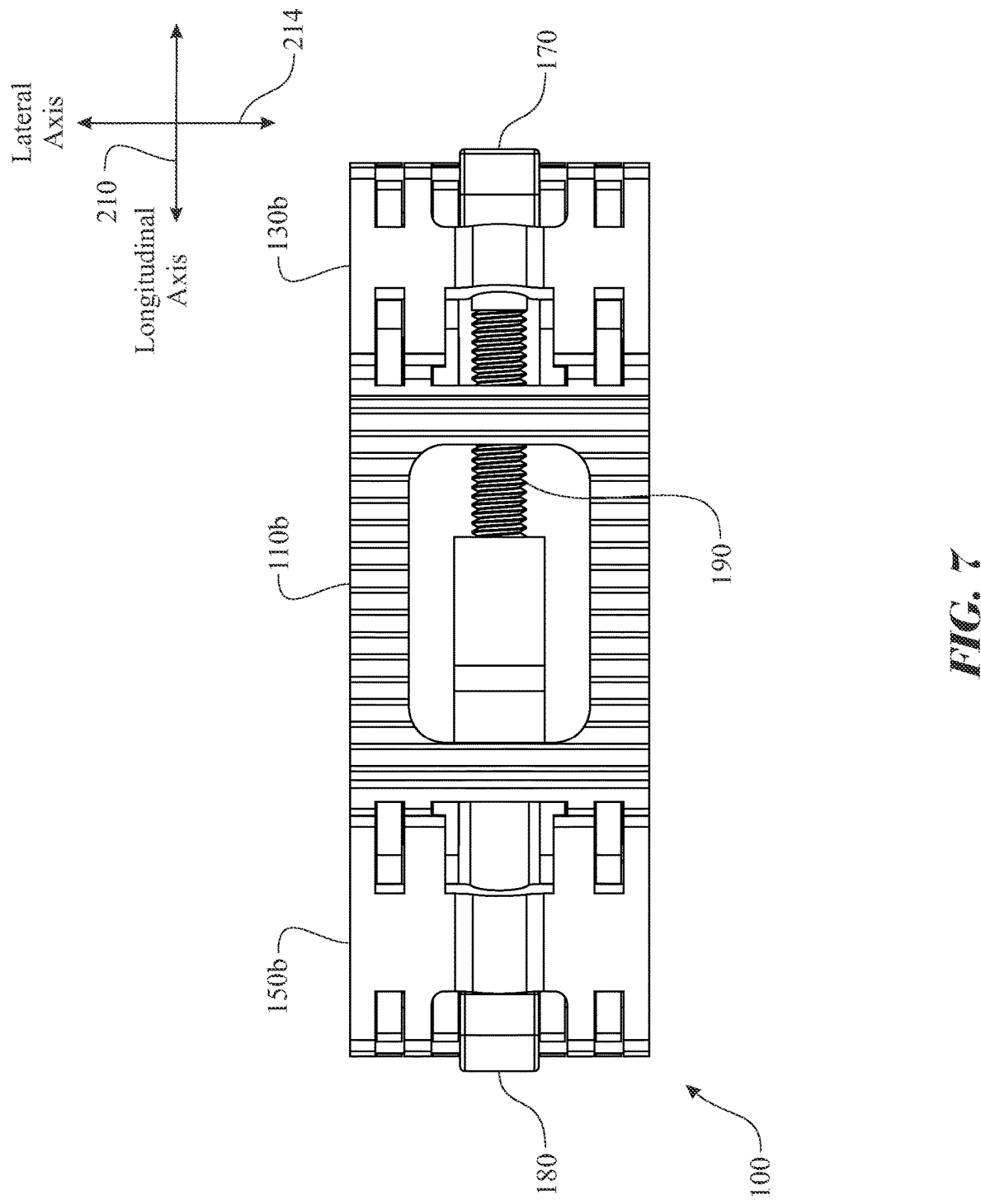
FIG. 7 presents a top plan view of the exemplary surgically implantable spacer, originally introduced in FIG. 1.

Details of each of the components of the surgically implantable spacer 100 are provided in enlarged views presented in FIGS. 4 through 6.

A central portion of the surgically implantable spacer 100 is presented in FIG. 5. The central portion includes a lower central disc replacement saddle member 110a and an upper central disc replacement saddle member 110b. Like elements of the lower central disc replacement saddle member 110a and the upper central disc replacement saddle member 110b are numbered the same, but specified by a suffix. Elements of the first or lower central disc replacement saddle member 110a are identified by a suffix "a". Elements of the second or upper central disc replacement saddle member 110b are identified by a suffix "b". The description herein references the first or lower central disc replacement saddle member 110a. The same description is representative of or applied to the second or upper central disc replacement saddle member 110b. The lower central disc replacement saddle member 110a includes a lower central disc replacement saddle body 112a. The lower central disc replacement saddle body 112a includes an exterior, joint contacting surface. The lower central disc replacement saddle body 112a is preferably shaped having an outwardly arched exterior joint contacting surface 113a. The exterior joint contacting surface 113a can include a texturing to improve retention of the surgically implantable spacer 100 in position respective to the joint. The textured of the exterior joint contacting surface 113a can be any suitable texturing. In the exemplary illustration, the texturing is created by a scalloped surface comprising a series of alternating ridges and recesses arranged extending in a spatial arrangement. The ridges can be of any suitable formation. In the exemplary illustration, the ridges are shaped having a blunt edge and the recesses are of a semi-circular shape.

It is understood that the texture can be of any suitable shape. As illustrated, the scalloped surface comprising a series of alternating ridges and recesses arranged being parallel to one another in a spatial arrangement. As illustrated, the scalloped surface comprising a series of evenly spaced alternating ridges and recesses arranged being parallel to one another. As illustrated, the scalloped surface comprising a series of alternating ridges and recesses arranged being parallel to a lateral axis 212 in a spatial arrangement. In an alternative arrangement, the texture can include a series of cross hatched formations, wherein the alternating recesses and ridges are arranged in both a first direction and a second direction. In another alternative arrangement, the texture can include a series of cross hatched formations, wherein the alternating recesses and ridges are arranged in both of a first direction and a second direction, the first angle and the second angle being different from one another. In another alternative arrangement, the texture can include a series of cross hatched formations, wherein the alternating recesses and ridges are arranged in both of a first direction and a second direction, the first angle and the second angle being perpendicular to one another. In another alternative arrangement, the texture can include a random surface formation. In another alternative arrangement, the texture can include a roughed surface formation. These are examples of textures. It is understood that any suitable texture can be provided on the exterior joint contacting surface 113a.

A lower central disc replacement saddle body central clearance 122a can be formed through the lower central disc replacement saddle body 112a. The lower central disc replacement saddle body central clearance 122a is preferably centrally located respective to the shape of the joint contacting surface 113a of the lower central disc replacement saddle body 112a. A lower central disc replacement saddle contraction element clearance 120a can be formed on an interior surface of the lower central disc replacement saddle body 112a (surface opposite of the lower central disc replacement saddle body joint contact surface 113a), wherein the lower central disc replacement saddle contraction element clearance 120a is of a shape and size to provide a clearance for other elements, such as one or more portions of the distal control arm rotational pivot shaft member 180.

The lower central disc replacement saddle member 110a includes features enabling a pivotal relationship between the lower central disc replacement saddle member 110a and the lower proximal expansion control arm member 130a on a proximal side thereof and a pivotal relationship between the lower central disc replacement saddle member 110a and the lower distal expansion control arm member 150a on a distal side thereof. A lower central disc replacement saddle first proximal hinge connecting formation 114a and a lower central disc replacement saddle second proximal hinge connecting formation 115a are provided on a proximal edge of the lower central disc replacement saddle member 110a. A lower central disc replacement saddle first distal hinge connecting formation 116a and a lower central disc replacement saddle second distal hinge connecting formation 117a are provided on a distal edge of the lower central disc replacement saddle member 110a. The exemplary illustration presents the hinge connecting formations 114a, 115a, 116a, 117a as elements having a semi-circular exterior or peripheral surface. Each of the hinge connecting formations 114a, 115a, 116a, 117a can include a lower central disc replacement saddle hinge connecting formation interlocking gap 118a extending longitudinally inward creating a pair of parallelly arranged semi-circular elements having the lower central disc replacement saddle hinge connecting formation interlocking gap 118a therebetween. Each of the hinge connecting formations 114a, 115a, 116a, 117a are arranged to enable a pivotal motion about the lateral axis 212.

A distal portion of the surgically implantable spacer 100 is presented in FIG. 4. The distal portion includes a lower distal expansion control arm member 150a, an upper distal expansion control arm member 150b and a distal control arm rotational pivot shaft member 180. Like elements of the lower distal expansion control arm member 150a and the upper distal expansion control arm member 150b are numbered the same, but specified by a suffix. Elements of the first or lower distal expansion control arm member 150a are identified by a suffix "a". Elements of the second or upper distal expansion control arm member 150b are identified by a suffix "b". The description herein references the first or lower distal expansion control arm member 150a. The same description is representative of or applied to the second or upper distal expansion control arm member 150b.

The lower distal expansion control arm member 150a includes a pair of lower distal expansion control arm sections 152a spaced apart by a lower distal expansion control arm bridge segment 160a. Each lower distal expansion control arm section 152a preferably extends in a direction parallel to the longitudinal axis 210. The lower distal expansion control arm member 150a includes features enabling a pivotal relationship between the lower central disc replacement saddle member 110a and the lower distal expansion control arm member 150a on a proximal side thereof and a pivotal relationship between the distal control arm rotational pivot shaft member 180 and the lower distal expansion control arm member 150a on a distal side thereof. A lower distal expansion control arm first central hinge connecting formation 154a and a lower distal expansion control arm second central hinge connecting formation 155a are provided on a proximal end of the lower distal expansion control arm member 150a. A lower distal expansion control arm first distal hinge connecting formation 156a and a lower distal expansion control arm second distal hinge connecting formation 157a are provided on a distal end of the lower distal expansion control arm member 150a. The exemplary illustration presents the hinge connecting formations 154a, 155a, 156a, 157a as elements having a semi-circular interior surface. Each of the hinge connecting formations 154a, 155a, 156a, 157a can include a lower distal expansion control arm hinge connecting formation interlocking gap 158a extending longitudinally inward creating a pair of parallelly arranged semi-circular elements having the lower distal expansion control arm hinge connecting formation interlocking gap 158a therebetween. Each of the hinge connecting formations 154a, 155a, 156a, 157a are arranged to enable a pivotal motion about the lateral axis 212.

The lower distal expansion control arm member 150*a* further comprises a lower distal expansion control arm transverse assembly retention element 164*a*. The lower distal expansion control arm transverse assembly retention element 164*a* retains an assembly between the lower distal expansion control arm member 150*a* and the lower central disc replacement saddle member 110*a* in a direction parallel to the lateral axis 212. Although the majority of the elements of the lower distal expansion control arm member 150*a* and the upper distal expansion control arm member 150*b* are the same, the exemplary lower distal expansion control arm transverse assembly retention element 164*a* is located on an exterior portion of each of the lower distal expansion control arm first central hinge connecting formation 154*a* and the lower distal expansion control arm second central hinge connecting formation 155*a* and the exemplary upper distal expansion control arm transverse assembly retention element 164*b* is located on an interior portion of each of the upper distal expansion control arm first central hinge connecting formation 154*b* and the upper distal expansion control arm second central hinge connecting formation 155*b*. The lower distal expansion control arm transverse assembly retention element 164*a* is designed and located to partially cover a central void defined by the interior semicircular shaped surface of the respective lower distal expansion control arm first central hinge connecting formation 154*a* or lower distal expansion control arm second central hinge connecting formation 155*a*. In the exemplary illustrations, the lower distal expansion control arm transverse assembly retention element 164*a* laterally retains the lower central disc replacement saddle first distal hinge connecting formation 116*a* and the lower central disc replacement saddle second distal hinge connecting formation 117*a* within the lower distal expansion control arm first central hinge connecting formation 154*a* and the lower distal expansion control arm second central hinge connecting formation 155*a* respectively.

The lower distal expansion control arm member 150*a* further comprises a lower distal expansion control arm contraction element clearance 162*a* formed generally oriented in a direction parallel to the longitudinal axis 210. The lower distal expansion control arm contraction element clearance 162*a* is of a size and shape to provide clearance for elements of the distal control arm rotational pivot shaft member 180, such as a distal control arm connecting shaft 183.

The distal control arm rotational pivot shaft member 180 can be of any suitable design. The distal control arm rotational pivot shaft member 180 provides two primary functions: (1) providing pivotal functionality for each of the lower distal expansion control arm member 150*a* and the upper distal expansion control arm member 150*b* and (2) drawing the proximal end and the distal end of the surgically implantable spacer 100 towards one another during use. The exemplary distal control arm rotational pivot shaft member 180 includes a pair of distal control arm rotational pivot shafts 188, each distal control arm rotational pivot shaft 188 extending outward from a distal control arm distal end block 182 in axial alignment and in a direction parallel to the lateral axis 212, wherein the pair of distal control arm rotational pivot shafts 188 provides a pivotal functionality for each of the lower distal expansion control arm member 150*a* and the upper distal expansion control arm member 150*b*. The pair of distal control arm rotational pivot shafts 188 extends outward from respective sidewalls of the distal control arm distal end block 182, where the sidewalls are larger than the diameter of the distal control arm rotational pivot shafts 188. The exemplary distal control arm rotational pivot shaft member 180 further comprises a threaded member receiving block 181, wherein the threaded member receiving block 181 provides a function of drawing the proximal end and the distal end of the surgically implantable spacer 100 towards one another during use. A threaded bore 184 is formed extending inward from a proximal end of the threaded member receiving block 181. The threaded bore 184 is of a depth enabling maximum contraction between the proximal end of the surgically implantable spacer 100 and the distal end of the surgically implantable spacer 100. A distal control arm connecting shaft 183 spatially connects the threaded member receiving block 181 and the distal control arm distal end block 182 to one another. The exemplary distal control arm connecting shaft 183 has a circular cross sectional shape and is designed to fit within the lower distal expansion control arm contraction element clearance 162*a* of the lower distal expansion control arm member 150*a* and the upper distal expansion control arm contraction element clearance 162*b* of the upper distal expansion control arm member 150*b*. A distal end of the threaded member receiving block 181 clears a proximal end of the lower distal expansion control arm bridge segment 160*a* and a proximal end of the upper distal expansion control arm bridge segment 160*b*.

The exemplary distal control arm rotational pivot shaft member 180 includes a pair of installation aiding groove 185, which can be utilized in conjunction with an insertion tool for a process of inserting the surgically implantable spacer 100 into position within the joint. In the exemplary illustration, each installation aiding groove 185 is a groove running parallel to the lateral axis 212. It is understood that any suitable feature to aid in gripping and orienting the surgically implantable spacer 100 during installation can be integrated into any suitable location of the surgically implantable spacer 100. For example, a recess and/or a slot can be included in a sidewall of the 110*a* and/or the upper central disc replacement saddle member 110*b*. Similarly, a recess can be included in an outer surface of one or more of the central disc replacement saddle hinge connecting formations 114*b*, 115*b*, 116*b*, 117*b*.

A proximal portion of the surgically implantable spacer 100 is presented in FIG. 6. The proximal portion includes a lower proximal expansion control arm member 130*a*, a upper proximal expansion control arm member 130*b*, a proximal control arm rotational pivot shaft member 170 and a threaded control member 190. Like elements of the lower proximal expansion control arm member 130*a* and the upper proximal expansion control arm member 130*b* are numbered the same, but specified by a suffix. Elements of the first or lower proximal expansion control arm member 130*a* are identified by a suffix "a". Elements of the second or upper proximal expansion control arm member 130*b* are identified by a suffix "b". The description herein references the first or lower proximal expansion control arm member 130*a*. The same description is representative of or applied to the second or upper proximal expansion control arm member 130*b*.

The lower proximal expansion control arm member 130*a* includes a pair of lower proximal expansion control arm sections 132*a* spaced apart by a lower proximal expansion control arm bridge segment 140*a*. Each lower proximal expansion control arm section 132*a* preferably extends in a direction parallel to the longitudinal axis 210. The lower proximal expansion control arm member 130*a* includes features enabling a pivotal relationship between the lower central disc replacement saddle member 110*a* and the lower proximal expansion control arm member 130*a* on a distal side thereof and a pivotal relationship between the proximal control arm rotational pivot shaft member 170 and the lower proximal expansion control arm member 130*a* on a proximal side thereof. A lower proximal expansion control arm first central hinge connecting formation 134*a* and a lower proximal expansion control arm second central hinge connecting formation 135*a* are provided on a proximal end of the lower proximal expansion control arm member 130*a*. A lower proximal expansion control arm first proximal hinge connecting formation 136*a* and a lower proximal expansion control arm second proximal hinge connecting formation 137*a* are provided on a distal end of the lower proximal expansion control arm member 130*a*. The exemplary illustration presents the hinge connecting formations 134*a*, 135*a*, 136*a*, 137*a* as elements having a semi-circular interior surface. Each of the hinge connecting formations 134*a*, 135*a*, 136*a*, 137*a* can include a lower proximal expansion control arm hinge connecting formation interlocking gap 138*a* extending longitudinally inward creating a pair of parallelly arranged semi-circular elements having the lower proximal expansion control arm hinge connecting formation interlocking gap 138*a* therebetween. Each of the hinge connecting formations 134*a*, 135*a*, 136*a*, 137*a* are arranged to enable a pivotal motion about the lateral axis 212.

Figure 8:
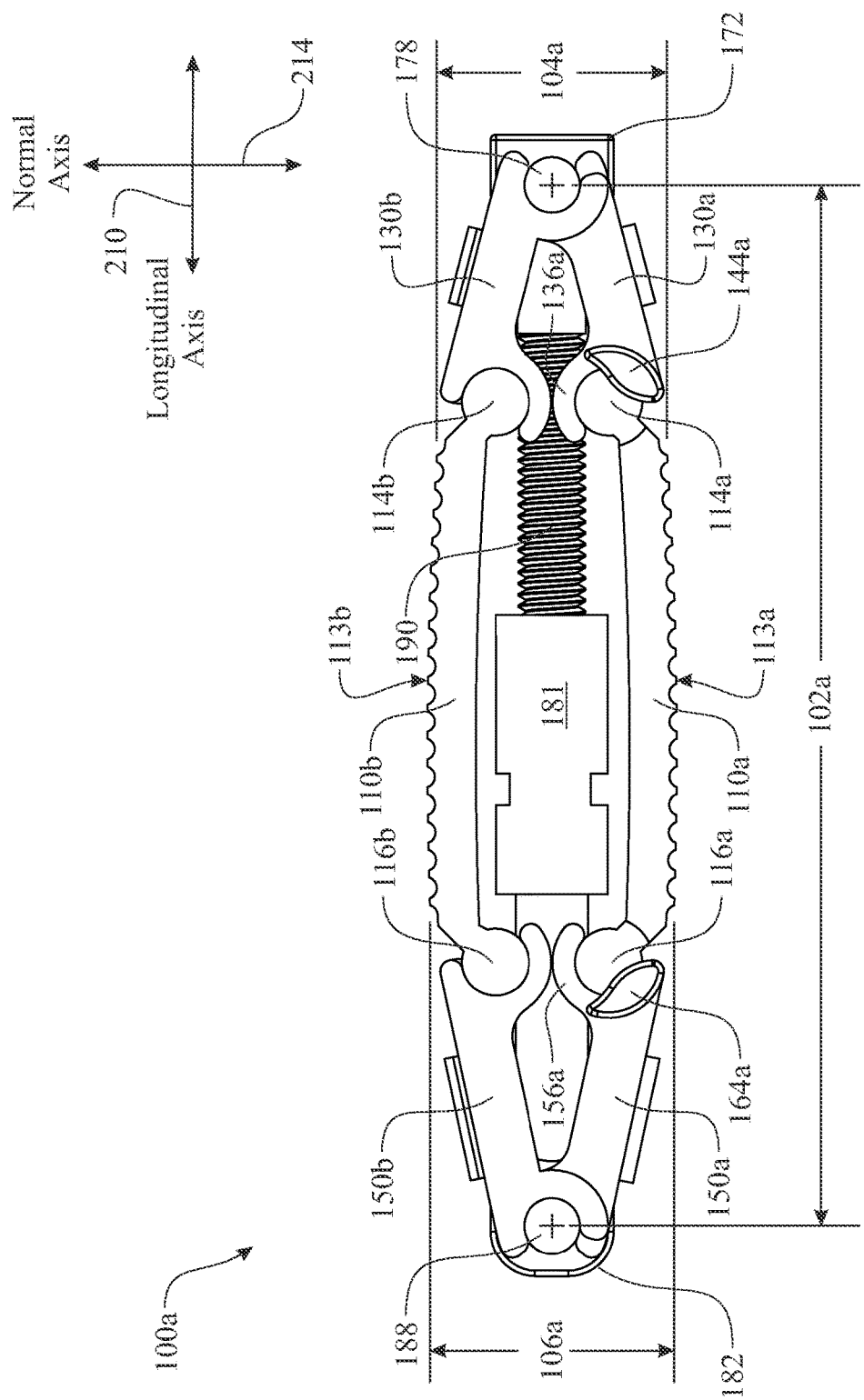
FIG. 8 presents a side elevation view of the exemplary surgically implantable spacer, originally introduced in FIG. 1, the surgically implantable spacer being shown in an insertion configuration.

The lower proximal expansion control arm member 130*a* further comprises a lower proximal expansion control arm transverse assembly retention element 144*a*. The lower proximal expansion control arm transverse assembly retention element 144*a* retains an assembly between the lower proximal expansion control arm member 130*a* and the lower central disc replacement saddle member 110*a* in a direction parallel to the lateral axis 212. Although the majority of the elements of the lower proximal expansion control arm member 130*a* and the upper proximal expansion control arm member 130*b* are the same, the exemplary lower proximal expansion control arm transverse assembly retention element 144*a* is located on an exterior portion of each of the lower proximal expansion control arm first proximal hinge connecting formation 136*a* and the lower proximal expansion control arm second proximal hinge connecting formation 137*a* and the exemplary upper proximal expansion control arm transverse assembly retention element 144*b* is located on an interior portion of each of the upper proximal expansion control arm first proximal hinge connecting formation 136*b* and the upper proximal expansion control arm second proximal hinge connecting formation 137*b*. The lower proximal expansion control arm transverse assembly retention element 144*a* is designed and located to partially cover a central void defined by the interior semi-circular shaped surface of the respective lower proximal expansion control arm first proximal hinge connecting formation 136*a* or lower proximal expansion control arm second proximal hinge connecting formation 137*a*. In the exemplary illustrations, the lower proximal expansion control arm transverse assembly retention element 144*a* laterally retains the lower central disc replacement saddle first proximal hinge connecting formation 114*a* and the lower central disc replacement saddle second proximal hinge connecting formation 115*a* within the lower proximal expansion control arm first proximal hinge connecting formation 136*a* and the lower proximal expansion control arm second proximal hinge connecting formation 137*a* respectively. The arrangement of the lower proximal expansion control arm transverse assembly retention element 144*a* is best shown in FIGS. 1 and 8.

The lower proximal expansion control arm member 130*a* further comprises a lower proximal expansion control arm contraction element clearance 142*a* formed generally oriented in a direction parallel to the longitudinal axis 210. The lower proximal expansion control arm contraction element clearance 142*a* is of a size and shape to provide clearance for elements of the threaded control member 190, such as a threaded control member threaded shank 198.

The proximal control arm rotational pivot shaft member 170 can be of any suitable design. The proximal control arm rotational pivot shaft member 170 provides two primary functions: (1) providing pivotal functionality for each of the lower proximal expansion control arm member 130*a* and the upper proximal expansion control arm member 130*b* and (2) drawing the proximal end and the distal end of the surgically implantable spacer 100 towards one another during use. The exemplary proximal control arm rotational pivot shaft member 170 includes a pair of proximal control arm rotational pivot shafts 178, each proximal control arm rotational pivot shaft 178 extending outward from a proximal control arm proximal end block 172 in axial alignment and in a direction parallel to the lateral axis 212, wherein the pair of proximal control arm rotational pivot shafts 178 provides a pivotal functionality for each of the lower proximal expansion control arm member 130*a* and the upper proximal expansion control arm member 130*b* at a proximal end thereof. A proximal control arm smooth walled bore 174 is formed extending inward from a proximal end of the proximal control arm proximal end block 172, terminating at a proximal control arm contraction element seating flange 176. The proximal control arm smooth walled bore 174 is of a depth enabling recession of a threaded control member drive head 192 of the threaded control member 190. The proximal control arm contraction element seating flange 176 is of a size that engages with a mating surface of a threaded control member seating flange 194 of the threaded control member 190, while including a bore for passage of the threaded control member threaded shank 198 therethrough. A depth of the proximal control arm smooth walled bore 174 can be slightly greater than a longitudinal dimension of the threaded control member drive head 192 (including the threaded control member seating flange 194), equal to the longitudinal dimension of the threaded control member drive head 192, or slightly shorter than the longitudinal dimension of the threaded control member drive head 192 (thus exposing a small portion of the threaded control member drive head 192).

The components 110*a*, 110*b*, 130*a*, 130*b*, 150*a*, 150*b*, 170, 180, 190 of the surgically implantable spacer 100 can be assembled in any reasonable order. The lower proximal expansion control arm member 130*a* is pivotally assembled to the proximal control arm rotational pivot shaft member 170 by snapping the lower proximal expansion control arm first central hinge connecting formation 134*a* to the first proximal control arm rotational pivot shaft member 178 of the proximal control arm rotational pivot shaft member 170 and snapping the lower proximal expansion control arm second central hinge connecting formation 135*a* to the second, opposite proximal control arm rotational pivot shaft 178 of the proximal control arm rotational pivot shaft member 170. The proximal control arm proximal end block 172 is positioned between the first lower proximal expansion control arm section 132*a* and the second lower proximal expansion control arm section 132*a*. The upper proximal expansion control arm member 130*b* is pivotally assembled to the proximal control arm rotational pivot shaft member 170 by snapping the upper proximal expansion control arm first central hinge connecting formation 134*b* to the first proximal control arm rotational pivot shaft 178 of the proximal control arm rotational pivot shaft member 170 and snapping the upper proximal expansion control arm second central hinge connecting formation 135b to the second, opposite proximal control arm rotational pivot shaft 178 of the proximal control arm rotational pivot shaft member 170. The proximal control arm proximal end block 172 is positioned between the first upper proximal expansion control arm section 132b and the second upper proximal expansion control arm section 132b.

One of the sections of the lower proximal expansion control arm first central hinge connecting formation 134a can be inserted into the upper proximal expansion control arm hinge connecting formation interlocking gap 138b of the upper proximal expansion control arm first central hinge connecting formation 134b and one of the sections of the upper proximal expansion control arm first central hinge connecting formation 134b can be inserted into the lower proximal expansion control arm hinge connecting formation interlocking gap 138a of the lower proximal expansion control arm first central hinge connecting formation 134a. Similarly, one of the sections of the lower proximal expansion control arm second central hinge connecting formation 135a can be inserted into the upper proximal expansion control arm hinge connecting formation interlocking gap 138b of the upper proximal expansion control arm second central hinge connecting formation 135b and one of the sections of the upper proximal expansion control arm second central hinge connecting formation 135b can be inserted into the lower proximal expansion control arm hinge connecting formation interlocking gap 138a of the lower proximal expansion control arm second central hinge connecting formation 135a. Essentially, the above describes a configuration where the first hinge features of the first expansion control arm member and the first hinge features of the second expansion control arm member are interlaced with one another, as best shown in FIG. 1.

The lower distal expansion control arm member 150a is pivotally assembled to the distal control arm rotational pivot shaft member 180 by snapping the lower distal expansion control arm first distal hinge connecting formation 156a to the first distal control arm rotational pivot shaft 188 of the distal control arm rotational pivot shaft member 180 and snapping the lower distal expansion control arm second distal hinge connecting formation 157a to the second, opposite distal control arm rotational pivot shaft 188 of the distal control arm rotational pivot shaft member 180. The distal control arm distal end block 182 is positioned between the first lower distal expansion control arm section 152a and the second lower distal expansion control arm section 152a. The upper distal expansion control arm member 150b is pivotally assembled to the distal control arm rotational pivot shaft member 180 by snapping the upper distal expansion control arm first distal hinge connecting formation 156b to the first distal control arm rotational pivot shaft 188 of the distal control arm rotational pivot shaft member 180 and snapping the upper distal expansion control arm second distal hinge connecting formation 157b to the second, opposite distal control arm rotational pivot shaft 188 of the distal control arm rotational pivot shaft member 180. The distal control arm distal end block 182 is positioned between the first upper distal expansion control arm section 152b and the second upper distal expansion control arm section 152b.

Figure 2:
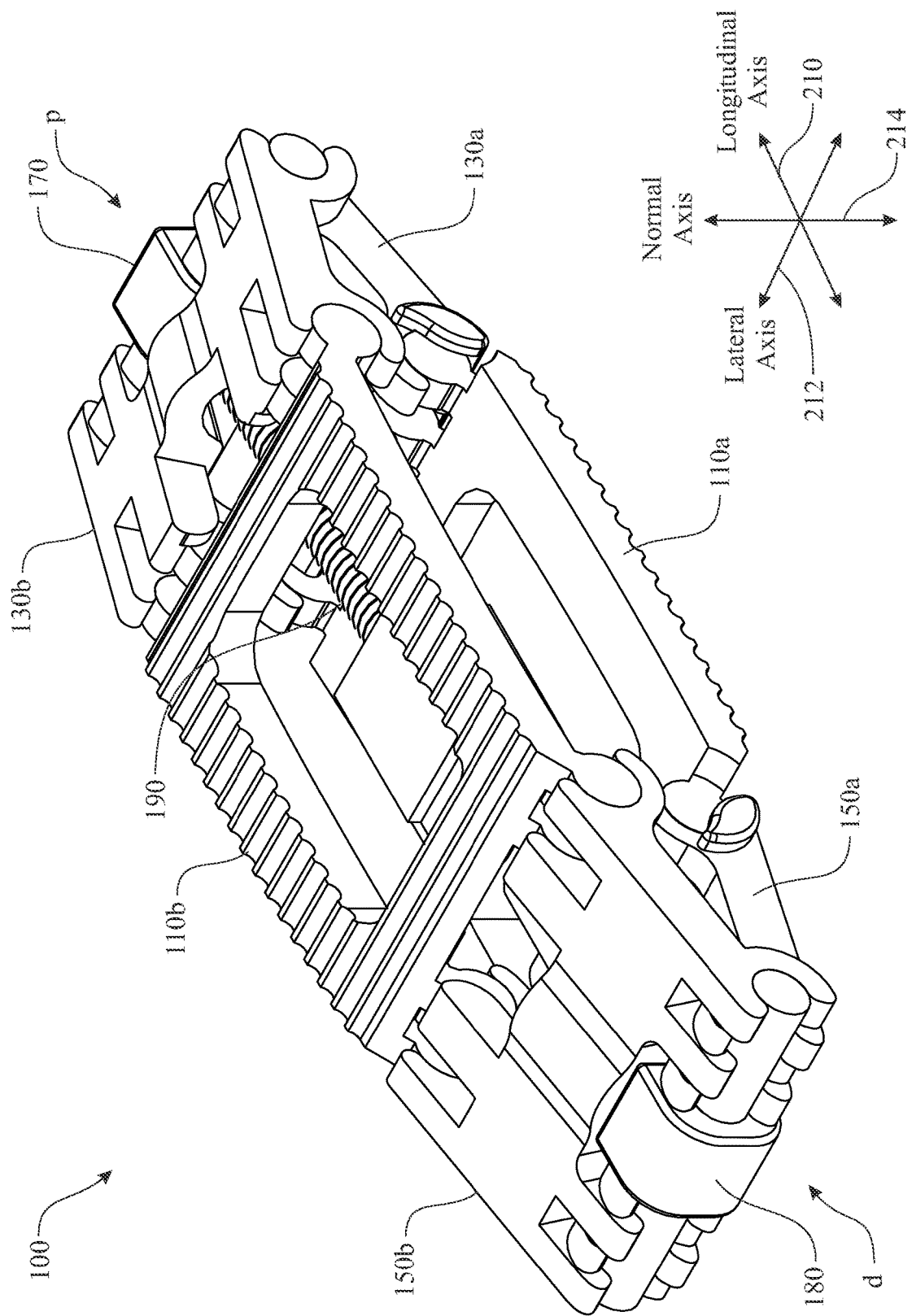
FIG. 2 presents an isometric top, side view of the exemplary surgically implantable spacer, originally introduced in FIG. 1 taken from a distal end, the surgically implantable spacer being shown in an insertion configuration.
Figure 3:
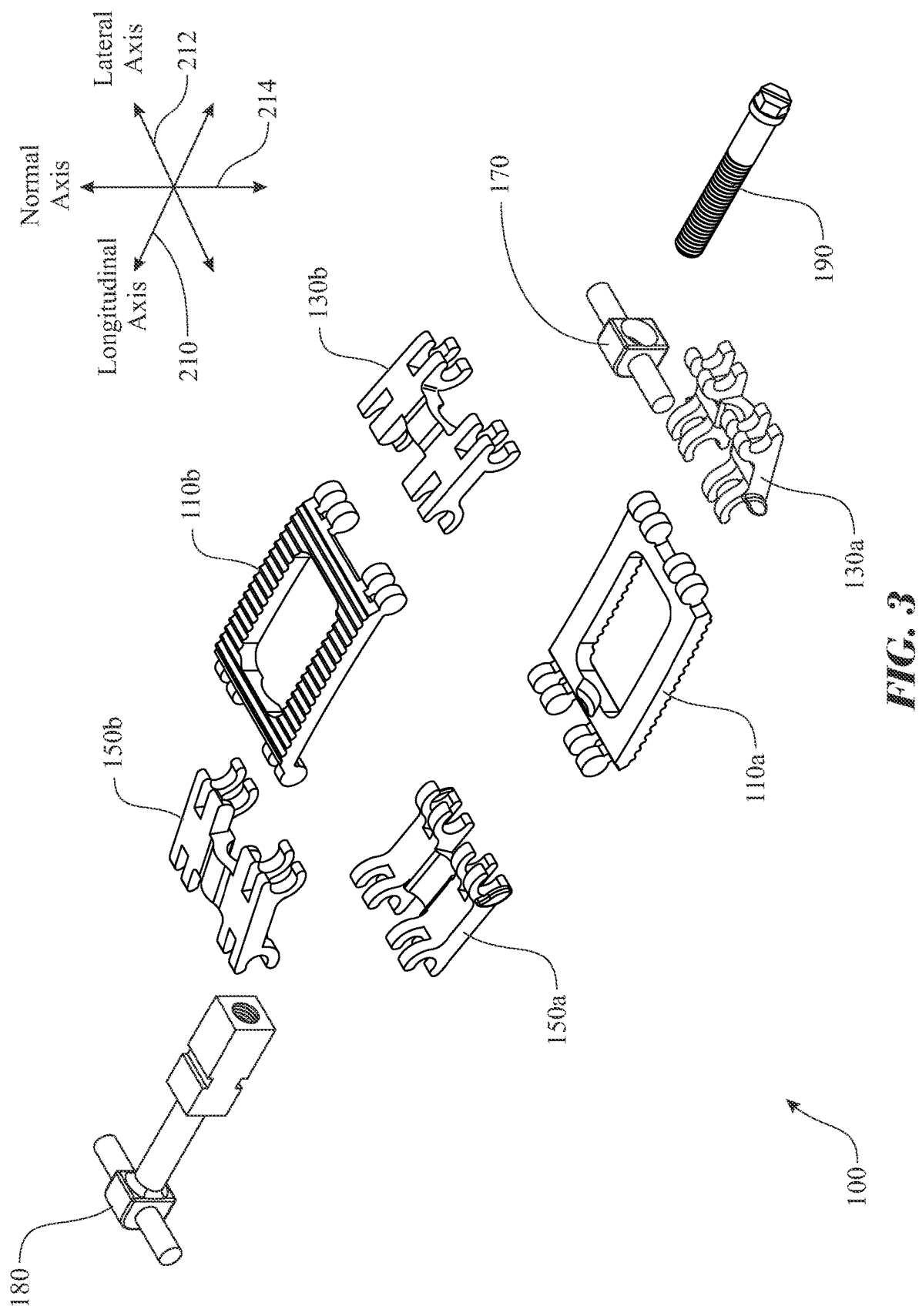
FIG. 3 presents an isometric top, side exploded assembly view of the surgically implantable spacer, originally introduced in FIG. 1, taken from a proximal end, the surgically implantable spacer being shown in a disassembled or preassembly configuration.

One of the sections of the lower distal expansion control arm first distal hinge connecting formation 156a can be inserted into the upper distal expansion control arm hinge connecting formation interlocking gap 158b of the upper distal expansion control arm first distal hinge connecting formation 156b and one of the sections of the upper distal expansion control arm first distal hinge connecting formation 156b can be inserted into the lower distal expansion control arm hinge connecting formation interlocking gap 158a of the lower distal expansion control arm first distal hinge connecting formation 156a. Similarly, one of the sections of the lower distal expansion control arm second distal hinge connecting formation 157a can be inserted into the upper distal expansion control arm hinge connecting formation interlocking gap 158b of the upper distal expansion control arm second distal hinge connecting formation 157b and one of the sections of the upper distal expansion control arm second distal hinge connecting formation 157b can be inserted into the lower distal expansion control arm hinge connecting formation interlocking gap 158a of the lower distal expansion control arm second distal hinge connecting formation 157a. Essentially, the above describes a configuration where the first hinge features of the first expansion control arm member and the first hinge features of the second expansion control arm member are interlaced with one another, as best shown in FIG. 2.

The distal control arm connecting shaft 183 of the distal control arm rotational pivot shaft member 180 would be positioned between the lower distal expansion control arm transverse assembly retention element 164a of the lower distal expansion control arm member 150a and the upper distal expansion control arm transverse assembly retention element 164b of the upper distal expansion control arm member 150b. The threaded member receiving block 181 is positioned between the first lower distal expansion control arm section 152a and the second lower distal expansion control arm section 152a of the lower distal expansion control arm member 150a and between the first upper distal expansion control arm section 152b and the second upper distal expansion control arm section 152b of the upper distal expansion control arm member 150b. The dimension of the lower distal expansion control arm bridge segment 160a along a direction parallel to the longitudinal axis 210 provides clearance for each of the threaded member receiving block 181 and the distal control arm distal end block 182. Similarly, the dimension of the upper distal expansion control arm bridge segment 160b along a direction parallel to the longitudinal axis 210 provides clearance for each of the threaded member receiving block 181 and the distal control arm distal end block 182. The straddling of the pair of lower distal expansion control arm sections 152a and the pair of upper distal expansion control arm section 152b about the distal control arm distal end block 182 retains the lower distal expansion control arm member 150a and the upper distal expansion control arm member 150b from moving in a direction parallel to the lateral axis 212.

The central components are then assembled to each of the proximal subassembly and the distal subassembly as described by the following.

The lower central disc replacement saddle member 110a is pivotally assembled to the lower proximal expansion control arm member 130a by snapping the lower central disc replacement saddle first proximal hinge connecting formation 114a of the lower central disc replacement saddle member 110a and the lower proximal expansion control arm first proximal hinge connecting formation 136a of the lower proximal expansion control arm member 130a to one another and snapping the lower central disc replacement saddle second proximal hinge connecting formation 115a of the lower central disc replacement saddle member 110a to the lower proximal expansion control arm second proximal hinge connecting formation 137a of the lower proximal expansion control arm member 130a to one another. Each of the lower proximal expansion control arm transverse assembly retention elements 144*a* restrains any movement of the lower central disc replacement saddle member 110*a* respective to the lower proximal expansion control arm member 130*a* in direction parallel to the lateral axis 212.

The upper central disc replacement saddle member 110*b* is pivotally assembled to the upper proximal expansion control arm member 130*b* by snapping the upper central disc replacement saddle first proximal hinge connecting formation 114*b* of the upper central disc replacement saddle member 110*b* and the upper proximal expansion control arm first proximal hinge connecting formation 136*b* of the upper proximal expansion control arm member 130*b* to one another and snapping the upper central disc replacement saddle second proximal hinge connecting formation 115*b* of the upper central disc replacement saddle member 110*b* to the upper proximal expansion control arm second proximal hinge connecting formation 137*b* of the upper proximal expansion control arm member 130*b* to one another. Each of the upper proximal expansion control arm transverse assembly retention elements 144*b* restrains any movement of the upper central disc replacement saddle member 110*b* respective to the upper proximal expansion control arm member 130*b* in direction parallel to the lateral axis 212.

When the surgically implantable spacer 100 is placed into an insertion configuration, one of the sections of the upper proximal expansion control arm first proximal hinge connecting formation 136*b* can be inserted into the lower proximal expansion control arm hinge connecting formation interlocking gap 138*a* of the lower proximal expansion control arm first proximal hinge connecting formation 136*a* and one of the sections of the lower proximal expansion control arm first proximal hinge connecting formation 136*a* can be inserted into the upper proximal expansion control arm hinge connecting formation interlocking gap 138*b* of the upper proximal expansion control arm first proximal hinge connecting formation 136*b*. Similarly, one of the sections of the upper proximal expansion control arm second proximal hinge connecting formation 137*b* can be inserted into the lower proximal expansion control arm hinge connecting formation interlocking gap 138*a* of the lower proximal expansion control arm second proximal hinge connecting formation 137*a* and one of the sections of the lower proximal expansion control arm second proximal hinge connecting formation 137*a* can be inserted into the upper proximal expansion control arm hinge connecting formation interlocking gap 138*b* of the upper proximal expansion control arm second proximal hinge connecting formation 137*b*. Essentially, the above describes a configuration where the first hinge features 136*a* of the first expansion control arm member 130*a* and the first hinge features 136*b* of the second expansion control arm member 130*b* are interlaced with one another, as best shown in FIG. 1.

The lower central disc replacement saddle member 110*a* is pivotally assembled to the lower distal expansion control arm member 150*a* by snapping the lower central disc replacement saddle first distal hinge connecting formation 116*a* of the lower central disc replacement saddle member 110*a* and the lower distal expansion control arm first central hinge connecting formation 154*a* of the lower distal expansion control arm member 150*a* to one another and snapping the lower central disc replacement saddle second distal hinge connecting formation 117*a* of the lower central disc replacement saddle member 110*a* to the lower distal expansion control arm second central hinge connecting formation 155*a* of the lower distal expansion control arm member 150*a* to one another. Each of the lower distal expansion control arm transverse assembly retention elements 164*a* restrains any movement of the lower central disc replacement saddle member 110*a* respective to the lower distal expansion control arm member 150*a* in direction parallel to the lateral axis 212. The arrangement of the lower proximal expansion control arm transverse assembly retention element 144*a* is best shown in FIG. 1.

The upper central disc replacement saddle member 110*b* is pivotally assembled to the upper distal expansion control arm member 150*b* by snapping the upper central disc replacement saddle first distal hinge connecting formation 116*b* of the upper central disc replacement saddle member 110*b* and the upper distal expansion control arm first central hinge connecting formation 154*b* of the upper distal expansion control arm member 150*b* to one another and snapping the upper central disc replacement saddle second distal hinge connecting formation 117*b* of the upper central disc replacement saddle member 110*b* to the upper distal expansion control arm second central hinge connecting formation 155*b* of the upper distal expansion control arm member 150*b* to one another. Each of the upper distal expansion control arm transverse assembly retention elements 164*b* restrains any movement of the upper central disc replacement saddle member 110*b* respective to the upper distal expansion control arm member 150*b* in direction parallel to the lateral axis 212.

When the surgically implantable spacer 100 is placed into an insertion configuration, one of the sections of the upper distal expansion control arm first central hinge connecting formation 154*b* can be inserted into the lower distal expansion control arm hinge connecting formation interlocking gap 158*a* of the lower distal expansion control arm first central hinge connecting formation 154*a* and one of the sections of the lower distal expansion control arm first central hinge connecting formation 154*a* can be inserted into the upper distal expansion control arm hinge connecting formation interlocking gap 158*b* of the upper distal expansion control arm first central hinge connecting formation 154*b*. Similarly, one of the sections of the upper distal expansion control arm second central hinge connecting formation 155*b* can be inserted into the lower distal expansion control arm hinge connecting formation interlocking gap 158*a* of the lower distal expansion control arm second central hinge connecting formation 155*a* and one of the sections of the lower distal expansion control arm second central hinge connecting formation 155*a* can be inserted into the upper distal expansion control arm hinge connecting formation interlocking gap 158*b* of the upper distal expansion control arm second central hinge connecting formation 155*b*. Essentially, the above describes a configuration where the first hinge features 154*a* of the first expansion control arm member 150*a* and the first hinge features 154*b* of the second expansion control arm member 150*b* are interlaced with one another, as best shown in FIG. 1.

The threaded control member threaded shank 198 is inserted into the proximal control arm smooth walled bore 174, passing through an aperture formed through the proximal control arm contraction element seating flange 176 and threadably assembled to the threaded bore 184 of the threaded member receiving block 181. The threaded control member 190 is rotated until a contacting surface of the threaded control member seating flange 194 contacts the mating surface of the proximal control arm contraction element seating flange 176 without drawing the proximal control arm rotational pivot shaft member 170 (i.e. the proximal control arm rotational pivot shaft 178) and the distal control arm rotational pivot shaft member 180 (i.e. the distal control arm rotational pivot shaft 188) towards one another. The threaded control member smooth shank 196 ensure against binding of the threaded control member 190 within the proximal control arm proximal end block 172.

Use of the surgically implantable spacer 100 is illustrated in FIGS. 8 through 13. The surgically implantable spacer 100 is illustrated as a surgically implantable spacer (installation configuration) 100*a* in FIG. 8. The surgically implantable spacer (installation configuration) 100*a* is a configuration where the distance or span between the proximal end of the surgically implantable spacer 100 (using the proximal control arm rotational pivot shaft 178 as a reference point) and the distal end of the surgically implantable spacer 100 (using the distal control arm rotational pivot shaft 188 as a reference point), where the distance or span is referred to as an operational span dimension (installation configuration) 102*a*. The dimensions of the surgically implantable spacer 100 are governed by two factors: (1) the distance or span between the proximal control arm rotational pivot shaft 178 and the distal control arm rotational pivot shaft 188 (identified by reference characters 102*a*, 102*b*, 102*c*, 102*d*, 102*e*) and resistance provided by the contacting surfaces of the joint.

The distance or span between the proximal control arm rotational pivot shaft 178 and the distal control arm rotational pivot shaft 188 (identified by reference characters 102*a*, 102*b*, 102*c*, 102*d*, 102*e*) is controlled by the threaded control member 190. The threaded control member 190 would be rotated 220 in a first direction (such as counter-clockwise) to expand the distance or span between the proximal control arm rotational pivot shaft 178 and the distal control arm rotational pivot shaft 188, wherein a surgically implantable spacer (installation configuration) 100*a* having an operational span dimension (installation configuration) 102*a* is presented in FIG. 8. The surgically implantable spacer (installation configuration) 100*a* has a respective distance or span between the lower central disc replacement saddle body joint contact surface 113*a* and the upper central disc replacement saddle body joint contact surface 113*b* at the proximal end (referred to as a proximal end vertebral contacting span dimension (installation configuration) 104*a*) and the distal end (referred to as a distal end vertebral contacting span dimension (installation configuration) 106*a*) that are the same.

Figure 9:
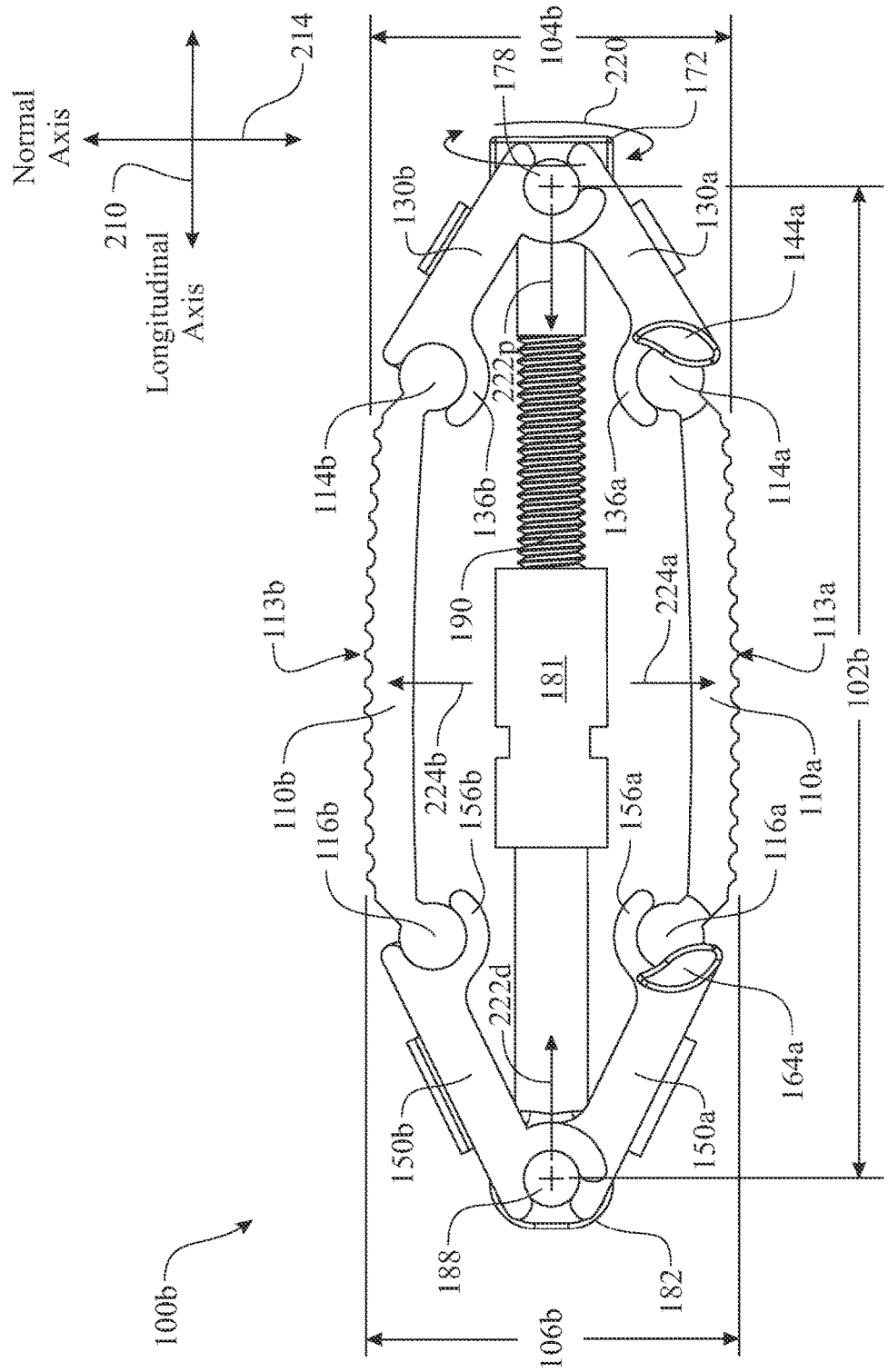
FIG. 9 presents a side elevation view of the exemplary surgically implantable spacer, originally introduced in FIG. 1, the surgically implantable spacer being shown in an initial vertebral contact configuration.
Figure 10:
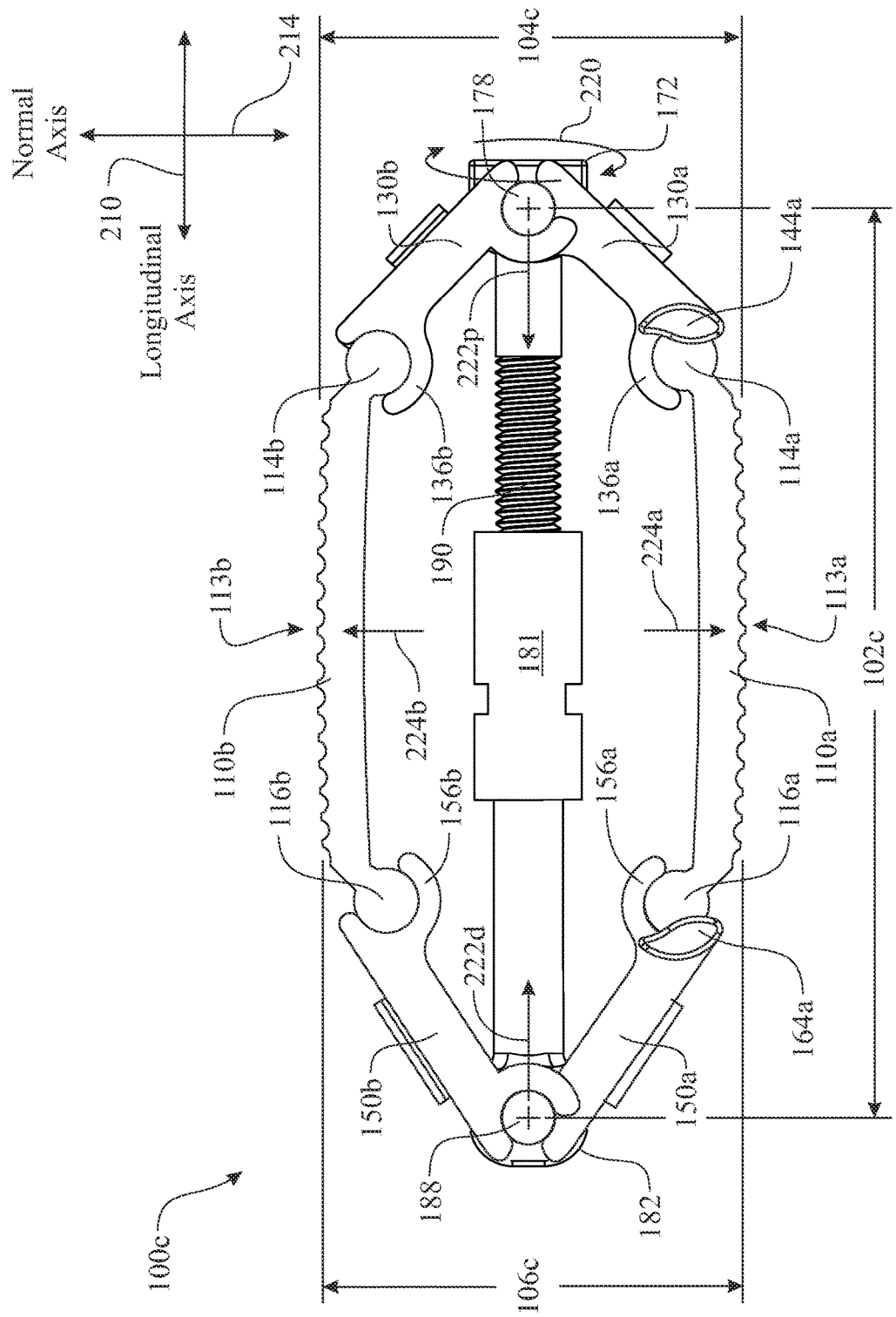
FIG. 10 presents a side elevation view of the exemplary surgically implantable spacer, originally introduced in FIG. 1, the surgically implantable spacer being shown in an expanded vertebral contact configuration, as a point where a resistance force at a first end of the spacer is greater than a resistance force at a second, opposite end of the spacer.

The threaded control member 190 would be rotated in a second direction (such as clockwise) to contract the distance or span between the proximal control arm rotational pivot shaft 178 and the distal control arm rotational pivot shaft 188. The illustrations present several states of a contracted surgically implantable spacer 100. A surgically implantable spacer (initial vertebral contact configuration) 100*b* having an operational span dimension (initial vertebral contact configuration) 102*b* is presented in FIG. 9. The initial contraction between the proximal control arm rotational pivot shaft 178 and the distal control arm rotational pivot shaft 188 is illustrated in FIG. 9, where the proximal control arm rotational pivot shaft 178 moves in accordance with a proximal rotational pivot shaft contraction motion 222*p* and the distal control arm rotational pivot shaft 188 moves in accordance with a distal rotational pivot shaft contraction motion 222*d*. In this configuration, the lower central disc replacement saddle body joint contact surface 113*a* and the upper central disc replacement saddle body joint contact surface 113*b* are not yet contacting the surfaces of the joint, thus enabling free movement of the lower central disc replacement saddle member 110*a* and the upper central disc replacement saddle member 110*b*. The contraction between the proximal control arm rotational pivot shaft 178 and the distal control arm rotational pivot shaft 188 causes the lower central disc replacement saddle member 110*a* to move in accordance with a lower central disc replacement saddle member expansion motion 224*a* and the upper central disc replacement saddle member 110*b* to move in accordance with a upper central disc replacement saddle member expansion motion 224*b*. During this condition (no resistance from the surfaces of the joint), the movement of the lower central disc replacement saddle member 110*a* and the upper central disc replacement saddle member 110*b* are even or symmetric with one another. The contraction continues between the proximal control arm rotational pivot shaft 178 and the distal control arm rotational pivot shaft 188 causing the lower central disc replacement saddle member 110*a* to continue to move in accordance with a lower central disc replacement saddle member expansion motion 224*a* and the upper central disc replacement saddle member 110*b* to continue to move in accordance with a upper central disc replacement saddle member expansion motion 224*b*. During this condition (no resistance from the surfaces of the joint), the movement of the lower central disc replacement saddle member 110*a* and the upper central disc replacement saddle member 110*b* continues to be even or symmetric with one another, moving the proximal control arm rotational pivot shaft 178 and the distal control arm rotational pivot shaft 188 to a span of operational span dimension (initial joint resistance configuration) 102*c* as shown in FIG. 10.

Figure 11:
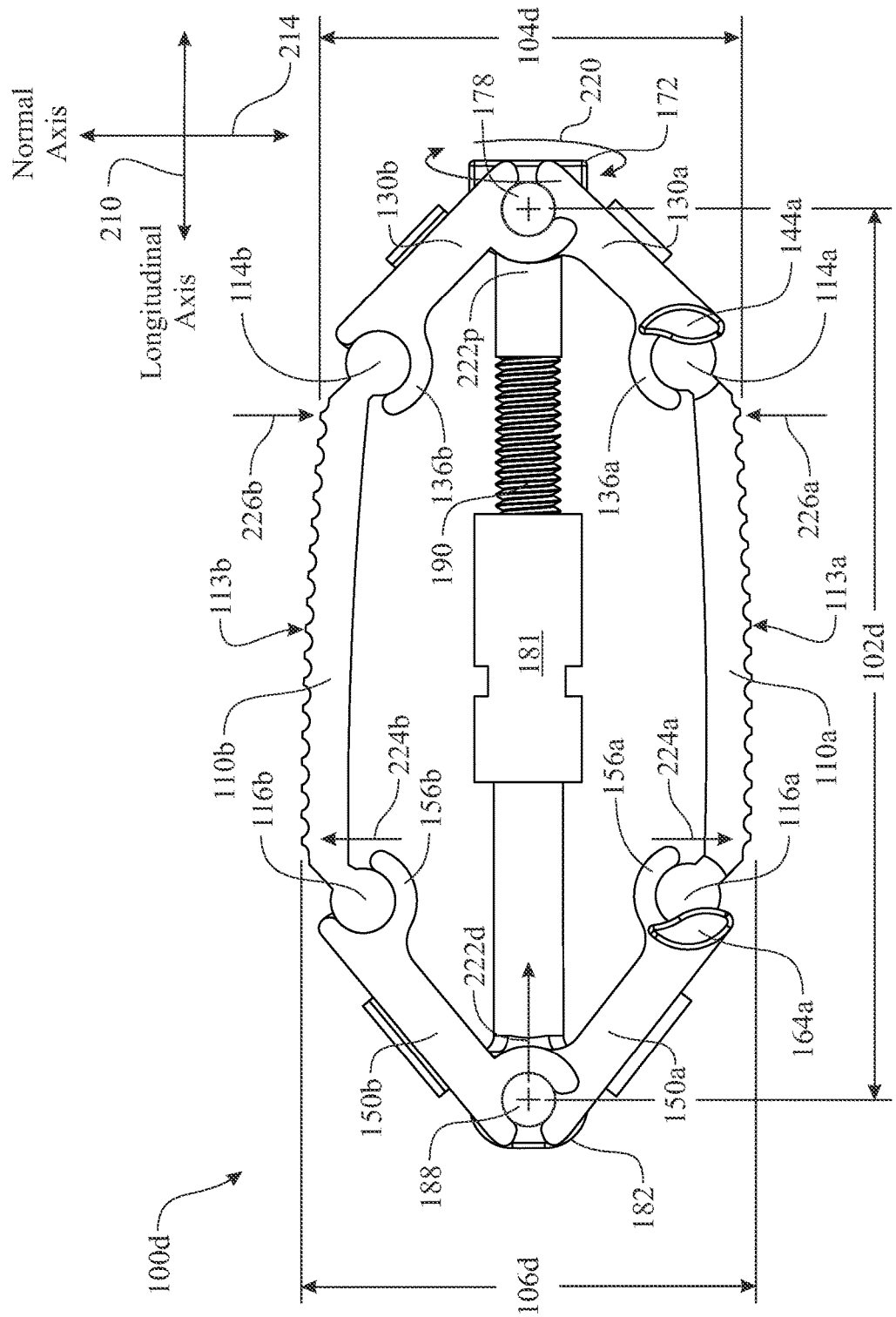
FIG. 11 presents a side elevation view of the exemplary surgically implantable spacer, originally introduced in FIG. 1, the surgically implantable spacer being shown in a final installation configuration.

As the surgically implantable spacer 100 continues to be subjected to contraction between the proximal control arm rotational pivot shaft 178 and the distal control arm rotational pivot shaft 188, the lower central disc replacement saddle body joint contact surface 113*a* and the upper central disc replacement saddle body joint contact surface 113*b* eventually are subjected to a resistance force 226*a*, 226*b*, as represented in FIG. 11. In FIG. 11, contact between the lower central disc replacement saddle body joint contact surface 113*a* and the respective resistive force provided by the surface of the joint is represented by a lower central disc replacement saddle member expansion resistance force 226*a* and contact between the upper central disc replacement saddle body joint contact surface 113*b* and the respective resistive force provided by the surface of the joint is represented by a upper central disc replacement saddle member expansion resistance force 226*b*. The resistive force 226*a*, 226*b* is generated by one or more physiological structure element of the joint. In one example, a tendon can generate the resistive force 226*a*, 226*b*. As the proximal end vertebral contacting span dimension (initial joint resistance configuration) 104*c* and the distal end vertebral contacting span dimension (initial joint resistance configuration) 106*c* of the surgically implantable spacer 100 increase, the lower central disc replacement saddle member 110*a* and the upper central disc replacement saddle member 110*b* can contact the respective surfaces of the joint, forcing the bones to separate, the separation generates tension in the respective tendons that secure the bones in position. As the tendons are drawn taut, the tendons generate a resistive force to the bones, which in turn, create the resistive forces 226*a*, 226*b* which are applied to a respective end of the lower central disc replacement saddle member 110*a* the upper central disc replacement saddle member 110*b*.

Figure 12:
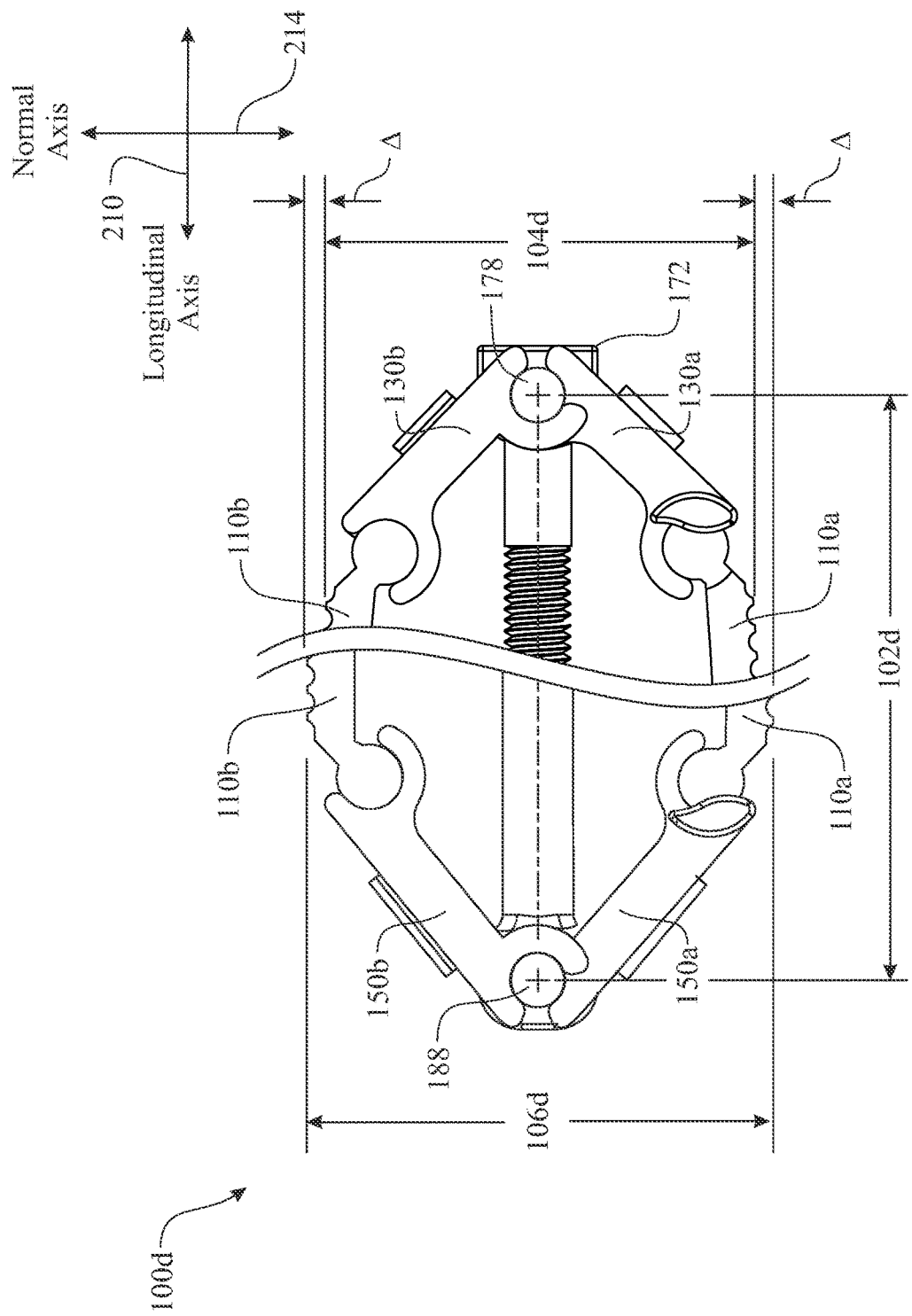
FIG. 12 presents a modified side elevation view of the exemplary surgically implantable spacer, in a configuration presented in FIG. 11, the illustration presenting an offset in expanded dimensions between a first end of the contacting surface and a second end of the contacting surface.

In the exemplary illustration, the lower central disc replacement saddle member expansion resistance force 226*a* is applied to a proximal end of the lower central disc replacement saddle body joint contact surface 113*a* and the upper central disc replacement saddle member expansion resistance force 226b is applied to a proximal end of the upper central disc replacement saddle body joint contact surface 113b. The distal end of the lower central disc replacement saddle body joint contact surface 113a and the distal end of the upper central disc replacement saddle body joint contact surface 113b remain free to expand outward in accordance with the lower central disc replacement saddle member expansion motion 224a and the upper central disc replacement saddle member expansion motion 224b respectively, positioning the lower central disc replacement saddle member 110a and the upper central disc replacement saddle member 110b into a non-parallel relation with one another. This motion continues until a similar scenario occurs at the opposite end of the lower central disc replacement saddle member 110a and the upper central disc replacement saddle member 110b. Upon reaching a condition where a resistive force (similar to the resistive force 226a, 226b but located on the opposite end of the lower central disc replacement saddle member 110a and the upper central disc replacement saddle member 110b) is generated at the opposite end of the lower central disc replacement saddle member 110a and the upper central disc replacement saddle member 110b, the expansion between the opposite end of the lower central disc replacement saddle member 110a and the upper central disc replacement saddle member 110b ceases. In this resulting configuration, as illustrated in FIGS. 11 and 12, the proximal end vertebral contacting span dimension (final installation configuration) 104d is less than the distal end vertebral contacting span dimension (final installation configuration) 106d. FIG. 12 by a dimension difference Δ.

Although the illustration presents a configuration where the proximal end is restrained, it is understood that the arrangement can be reversed, where the distal end is restrained and the proximal end vertebral contacting span dimension (final installation configuration) 104d becomes greater than the distal end vertebral contacting span dimension (final installation configuration) 106d.

In the exemplary embodiment, a length of the proximal expansion control arm member 130a, 130b is shorter than a length of the distal expansion control arm member 150a, 150b. To accommodate a joint where the arrangement is reversed, the surgically implantable spacer 100 can be assembled exchanging the shorter proximal expansion control arm member 130a, 130b and the longer distal expansion control arm member 150a, 150b.

Figure 13:
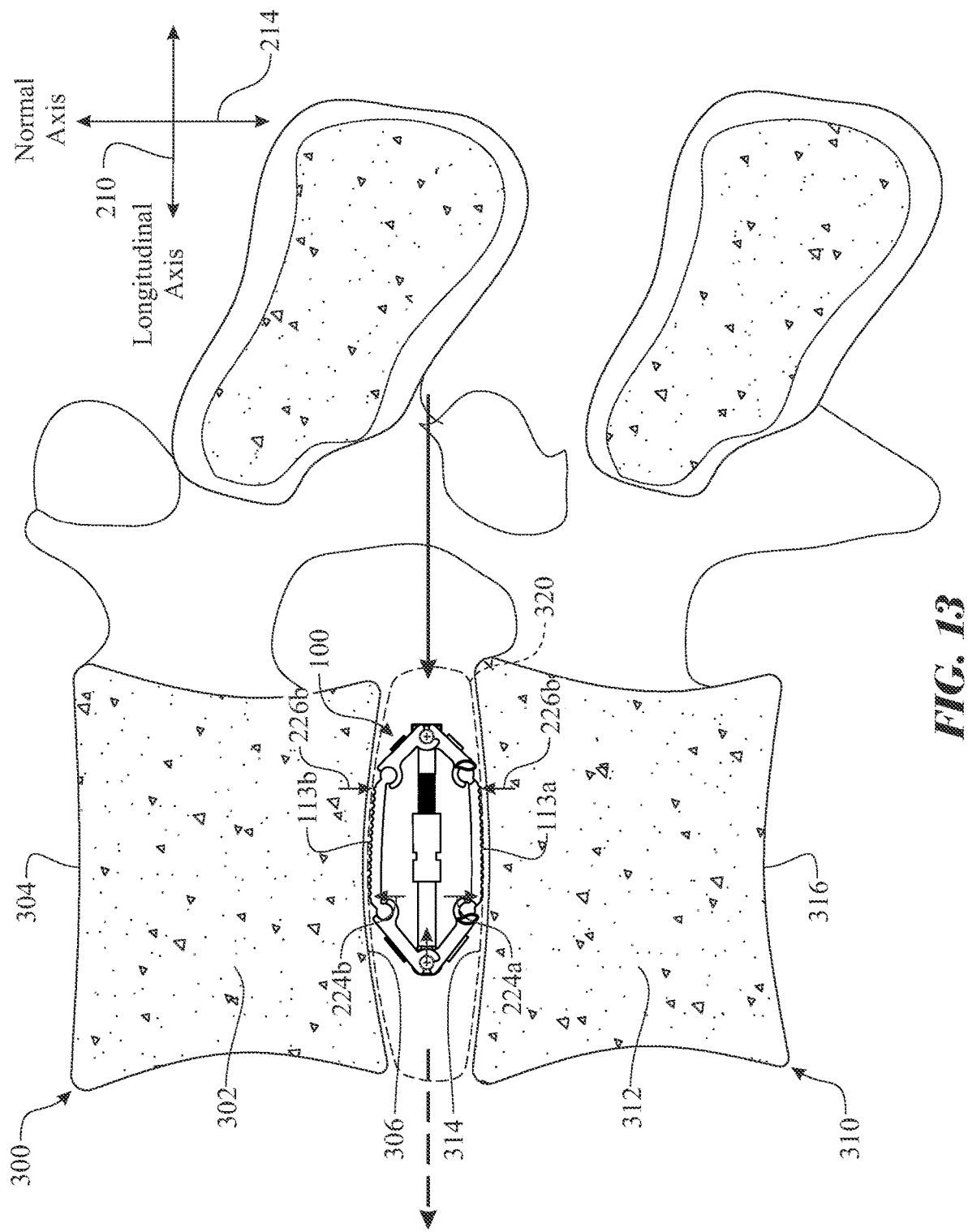
FIG. 13 presents a side elevation view of the exemplary surgically implantable spacer, originally introduced in FIG.

An exemplary installation of the surgically implantable spacer 100 into a joint is presented in an illustration shown in FIG. 13. In the exemplary implementation, the surgically implantable spacer 100 is utilized to replace an inter-vertebrae disc 320. The illustration presents a cross section of two adjacent vertebrae taken along a median plane. The exemplary joint is between a first joint member 300 and a second joint member 310. The first vertebrae 302 includes a first vertebrae first joint surface 304 on a first side and a first vertebrae second joint surface 306 on a second, opposite side. Similarly, the second vertebrae 312 includes a second vertebrae first joint surface 314 on a first side and a second vertebrae second joint surface 316 on a second, opposite side. More specifically, the joint is formed between the first vertebrae second joint surface 306 of the first vertebrae 302 and the second vertebrae second joint surface 314 of the second vertebrae 312. In the exemplary embodiment, the joint is prepared for insertion of the surgically implantable spacer 100 by removing the intra-vertebral disc 320 from between the first vertebrae second joint surface 306 of the first vertebrae 302 and the second vertebrae first joint surface 314 of the second vertebrae 312, in accordance with an intra-vertebral disc removal 322 (step 412 of FIG. 15), and replaced with the surgically implantable spacer 100.

Figure 14:
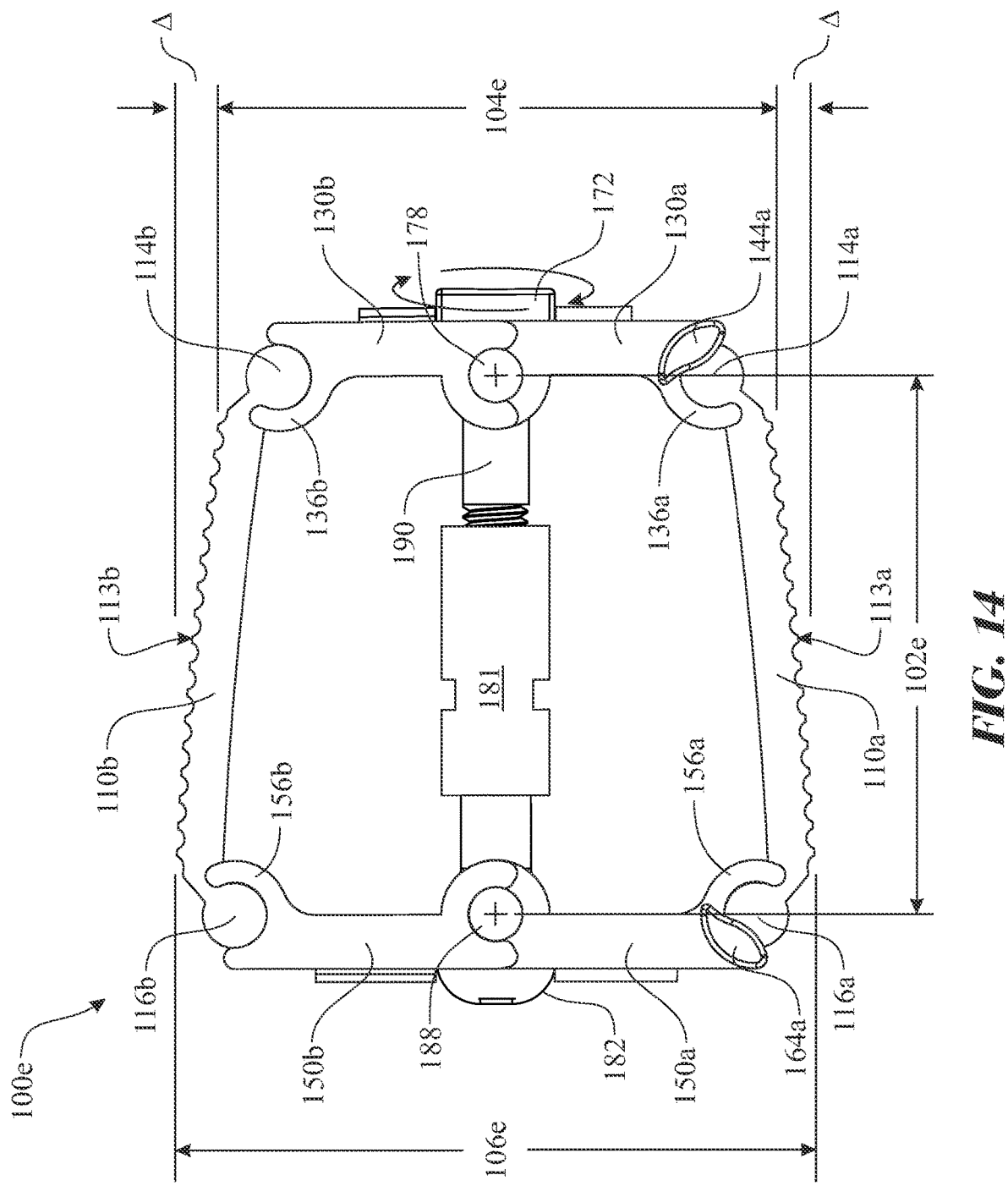
FIG. 14 presents a side elevation view of the exemplary surgically implantable spacer, originally introduced in FIG. 1, wherein the surgically implantable spacer being shown in a state of maximum extension.

The illustrations in FIGS. 8 through 13 present the surgically implantable spacer 100 in various configurations of expansion. As presented in FIGS. 8 through 13, the limitation on the expansion of the surgically implantable spacer 100 is provided by physiological limitations imposed upon the joint. In an alternative installation, the expansion can be limited by the dimensions of the elements of the surgically implantable spacer 100. The surgically implantable spacer 100 can be expanded into a configuration of a surgically implantable spacer (maximum expansion configuration) 100e, as illustrated in FIG. 14. In the configuration of the surgically implantable spacer (maximum expansion configuration) 100e, the lower proximal expansion control arm member 130a and the upper proximal expansion control arm member 130b are oriented into a linear arrangement, and, similarly, the lower distal expansion control arm member 150a and the upper distal expansion control arm member 150b are oriented into a linear arrangement. The linear arrangement of the lower proximal expansion control arm member 130a and the upper proximal expansion control arm member 130b, as well as the lower distal expansion control arm member 150a and the upper distal expansion control arm member 150b provides maximum separation between the lower central disc replacement saddle member 110a and the upper central disc replacement saddle member 110b. Since lengths of the proximal expansion control arm members 130a, 130b and the distal expansion control arm members 150a, 150b are different, a proximal end vertebral contacting span dimension (maximum expansion configuration) 104e and a distal end vertebral contacting span dimension (maximum expansion configuration) 106e differ from one another. In the exemplary illustration presented in FIG. 14, the lengths of the proximal expansion control arm members 130a, 130b are shorter than the lengths the distal expansion control arm members 150a, 150b, resulting in a configuration where the proximal end vertebral contacting span dimension (maximum expansion configuration) 104e is shorter than the distal end vertebral contacting span dimension (maximum expansion configuration) 106e.

Figure 15:
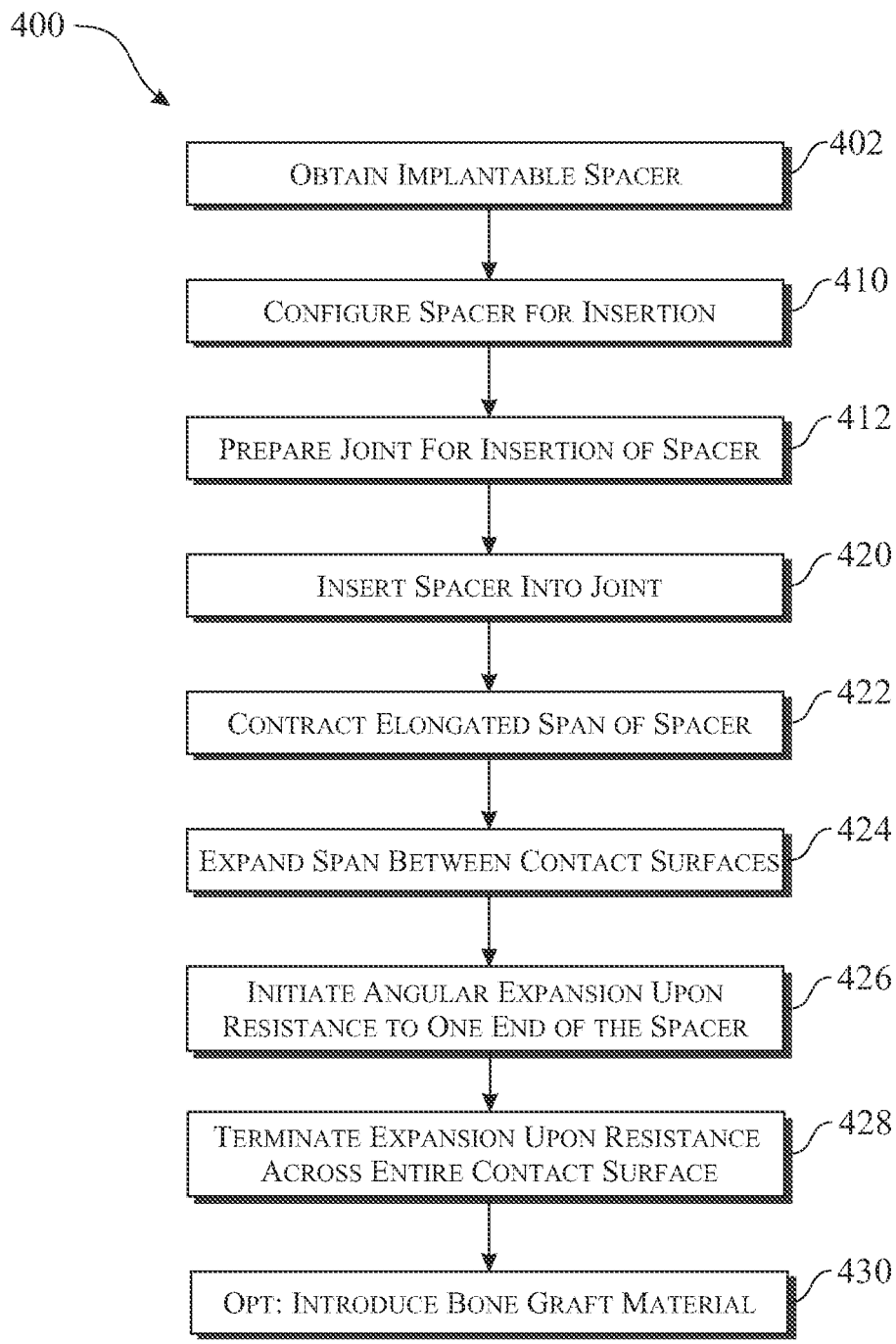
FIG. 15 presents an exemplary flow diagram describing a method of using the surgically implantable spacer.
Figure 16:
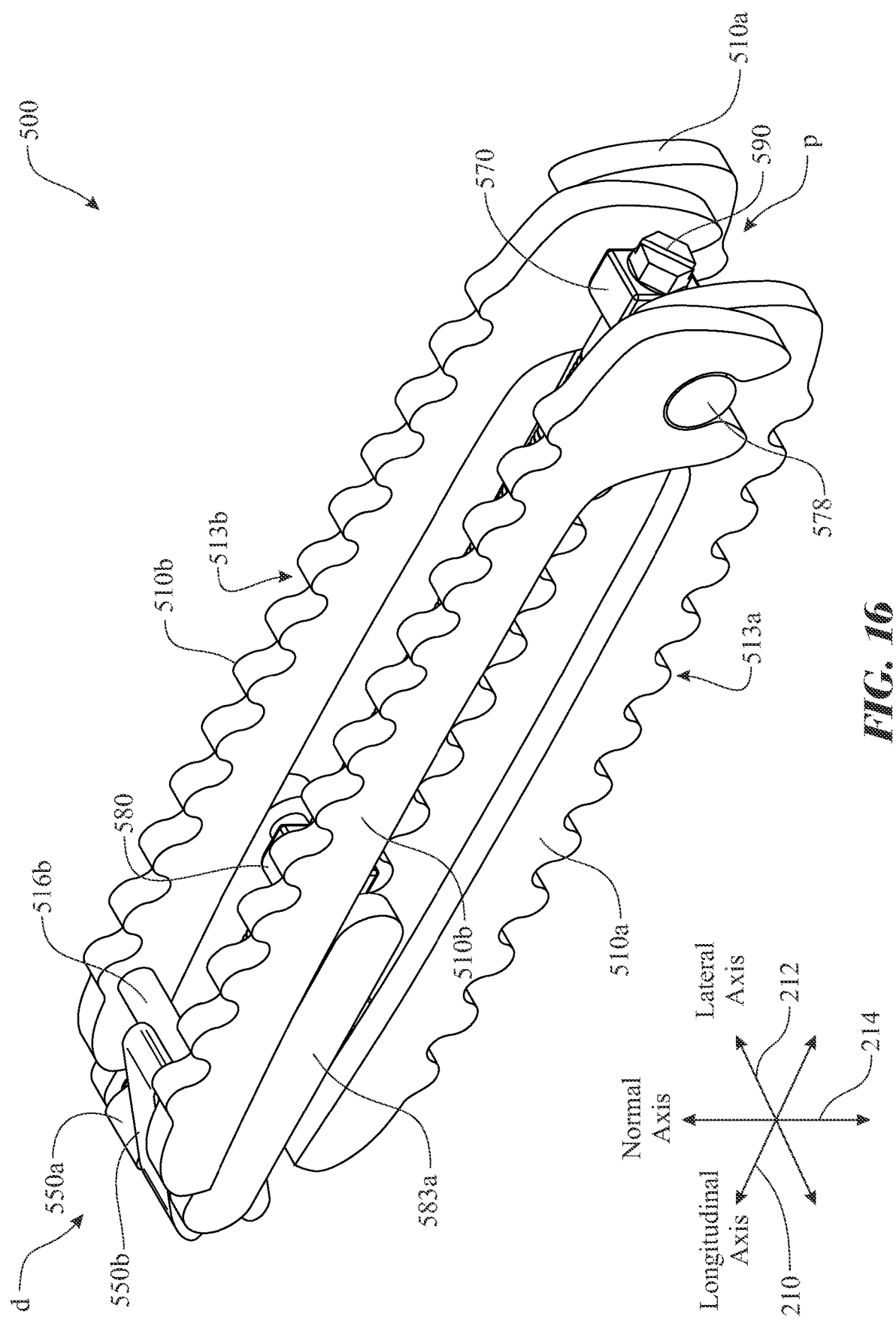
FIG. 16 presents an isometric top, side view of a simplified exemplary surgically implantable spacer taken from a proximal end, the surgically implantable spacer being shown in an insertion configuration, the illustration presenting a simplified variant of the surgically implantable spacer originally introduced in FIG. 1.
Figure 17:
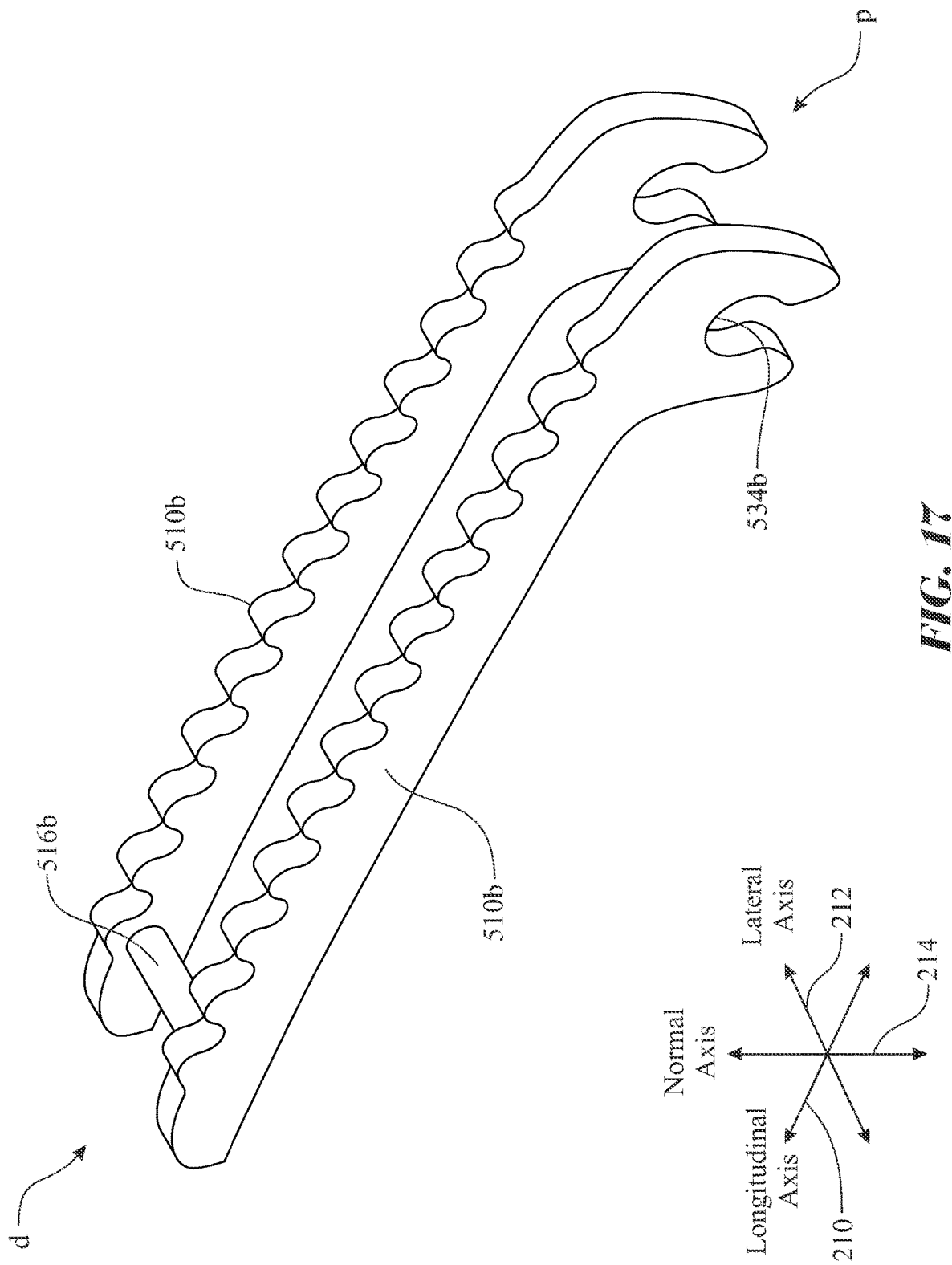
FIG. 17 presents an isometric top, side view of a second or upper disc replacement support truss of the simplified exemplary surgically implantable spacer originally introduced in FIG. 16.
Figure 18:
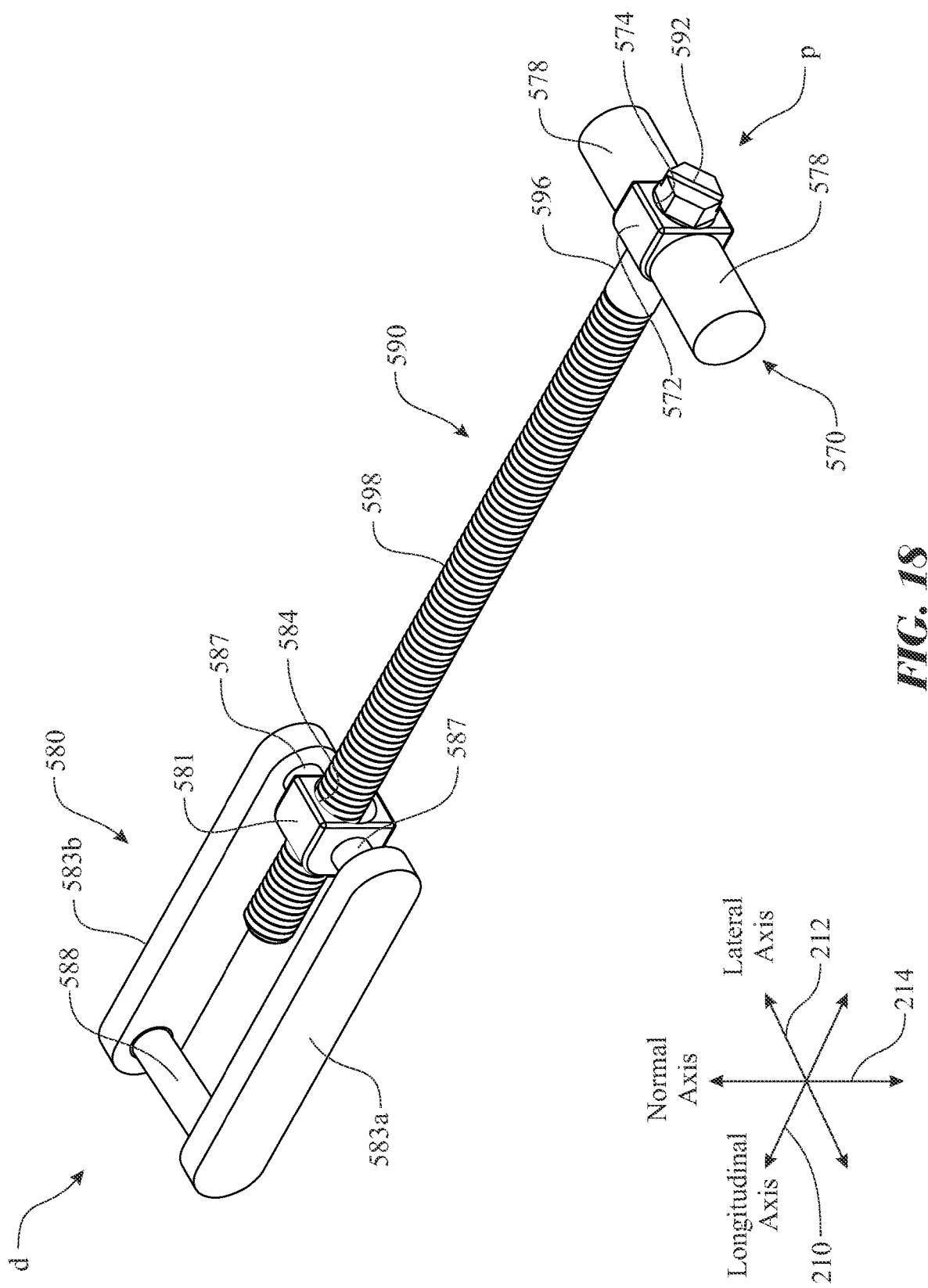
FIG. 18 presents an isometric top, side view of a expansion and contraction drive portion of the simplified exemplary surgically implantable spacer originally introduced in FIG. 16.

A method of installing and operating the surgically implantable spacer 100 is illustrated in FIGS. 8 through 13, with an associated flow diagram 400 being presented in FIG. 15. The surgically implantable spacer insertion flow diagram 400 initiates with a step of obtaining a surgically implantable spacer 100 (step 402). The surgically implantable spacer 100 can be configured to accommodate an angled installation by assembling a longer of the expansion control arm members 130a, 130b, 150a, 150b to the respective side of the surgically implantable spacer 100 requiring the larger of the proximal end vertebral contacting span dimension (final installation configuration) 104d or the distal end vertebral contacting span dimension (final installation configuration) 106d.

The span of the surgically implantable spacer 100 is extended to an insertion configuration, as shown in FIG. 8 (step 410). Upon preparation for surgery, the medical team would prepare the joint for insertion of the surgically implantable spacer (installation configuration) 100a (step 412). In the exemplary illustration, the intra-vertebral disc 320 is removed prior to installation of the surgically implantable spacer 100. Once the joint site is prepped, the surgically implantable spacer (installation configuration) 100a is inserted into the joint, between the first joint member 300 and the second joint member 310 (step 420). Once the surgically implantable spacer (installation configuration)

100*a* is properly located within the joint, the medical professional initiates a process of contracting the operational span dimension (installation configuration) 102*a* extending between the proximal control arm rotational pivot shaft 178 and the distal control arm rotational pivot shaft 188 (step 422). In the exemplary embodiment, the process of contracting the operational span dimension (installation configuration) 102*a* is accomplished by rotating 220 the threaded control member drive head 192 of the threaded control member 190 in a predetermined direction (clockwise in the exemplary illustration). The result of the step of contracting the operational span dimension (installation configuration) 102*a* causes the lower central disc replacement saddle member 110*a* and upper central disc replacement saddle member 110*b* to separate in manner retaining a substantially parallel arrangement, as illustrated in FIGS. 9 and 10. The separation between the lower central disc replacement saddle member 110*a* and the upper central disc replacement saddle member 110*b* is referenced by the proximal end vertebral contacting span dimension (initial vertebral contact configuration) 104*b* and the distal end vertebral contacting span dimension (initial vertebral contact configuration) 106*b* and subsequently the proximal end vertebral contacting span dimension (initial joint resistance configuration) 104*c* and the distal end vertebral contacting span dimension (initial joint resistance configuration) 106*c*. As illustrated in FIG. 9, the dimensions of proximal end vertebral contacting span dimension (initial vertebral contact configuration) 104*b* and distal end vertebral contacting span dimension (initial vertebral contact configuration) 106*b* are the same and as illustrated in FIG. 10, the dimensions of proximal end vertebral contacting span dimension (initial joint resistance configuration) 104*c* and distal end vertebral contacting span dimension (initial joint resistance configuration) 106*c* are the same. During installation, the lower central disc replacement saddle body joint contact surface 113*a* and the upper central disc replacement saddle body joint contact surface 113*b* can be in contact with a second vertebrae first joint surface 314 and a first vertebrae second joint surface 306 respectively. As the distance 104*c*, 106*c* between the lower central disc replacement saddle member 110*a* and the upper central disc replacement saddle member 110*b* increases (step 424), the lower central disc replacement saddle body joint contact surface 113*a* and the upper central disc replacement saddle body joint contact surface 113*b* drive the respective contacted bones of the joint in opposite directions from one another. The bones are restrained by one or more biological features. At some point in the expansion process (step 424), one end of each of the lower central disc replacement saddle member 110*a* and the upper central disc replacement saddle member 110*b* are subjected to a resistive force 226*a*, 226*b* respectively (step 426). The resistive force 226*a*, 226*b* can be generated by any physiological feature that retains the bones within a limited distance. In one example, the physiological feature can be tendons which restrain motion of one or more bones of the joint. In another example, the physiological feature can be muscles which restrain motion of one or more bones of the joint.

Once one end of the lower central disc replacement saddle body joint contact surface 113*a* and the upper central disc replacement saddle body joint contact surface 113*b* move a second vertebrae 312 and a first vertebrae 302 respectively to a position where separating motion of the first vertebrae 302 and the second vertebrae 312 at one end of the lower central disc replacement saddle member 110*a* and the upper central disc replacement saddle member 110*b* becomes limited or restricted, the restricted motion generates a resistance force 226*a* and 226*b* respectively. Upon being subjected to the resistance force 226*a*, 226*b* at one end of the surgically implantable spacer (initial joint resistance configuration) 100*c*, the continued contraction generated by the threaded control member 190 causes the non-restricted end to continue to expand outward, as illustrated in FIG. 11 resulting in a configuration where the lower central disc replacement saddle member 110*a* and the upper central disc replacement saddle member 110*b* are no longer parallel with one another (step 426). The contraction between the proximal control arm rotational pivot shaft 178 and the distal control arm rotational pivot shaft 188 continues, causing the unrestrained end of the lower central disc replacement saddle member 110*a* and the upper central disc replacement saddle member 110*b* to continue to expand until each of the lower central disc replacement saddle body joint contact surface 113*a* and the upper central disc replacement saddle body joint contact surface 113*b* are in full, restrained contact with the respective surfaces of the joint (step 428). The full, restrained condition would occur when the joint is separated to a position where, in addition to the currently imposed restrictions at the first end, physiological features restrict movement of the bones of the joint at the second opposite end. Once the surgically implantable spacer (final installation configuration) 100*d* is properly seated within the joint, in a condition where the joint is being fused, the medical team can introduce bone graft material within an interior of the surgically implantable spacer 100 (step 430).

The surgically implantable spacer 100 presents an exemplary configuration comprising a pair of control arm members 130*a*, 130*b*, 150*a*, 150*b*, assembled to each end thereof. It is also understood that a surgically implantable spacer 500 can be designed employing a pair of control arm members 550*a*, 550*b* at one end thereof, as illustrated in FIGS. 16 through 21.

The surgically implantable spacer 500 includes a pair of disc replacement support truss assemblies, more specifically, a first or lower disc replacement support truss assembly and a second or upper disc replacement support truss assembly. Each of the disc replacement support truss assemblies includes the same elements, using the second or upper disc replacement support truss assembly (detailed in FIG. 17) as an example. The elements of the second or upper disc replacement support truss assembly are identified by a suffix "b", whereas elements of the first or lower disc replacement support truss assembly are identified by a suffix "a".

Elements of the second or upper disc replacement support truss assembly include a near or first side upper disc replacement support truss 510*b* (located on a first or a left side of the assembly), a far or second side upper disc replacement support truss 510*b* (located on a second or a right side of the assembly) and an upper spanning control cross member 516*b* spanning between distal ends of the near or first side upper disc replacement support truss 510*b* (left) and the far or second side upper disc replacement support truss 510*b* (right). The second or upper disc replacement support truss spanning control cross member 516*b* is designed to provide a rotational interface between the disc replacement support truss assembly and a respective second or upper truss expansion control member 550*b*. A second or upper disc replacement support truss joint contact surface 513*b* of each second or upper disc replacement support truss 510*b* can be shaped to include features to aid in retention of the surgically implantable spacer 500 within a joint.

A second or upper disc replacement support truss pivot assembly formation 534*b* can be formed in a proximal end to provide a rotational interface between the disc replacement support truss assembly and a proximal control arm rotational pivot shaft member 570. In the exemplary illustration, each second or upper disc replacement support truss pivot assembly formation 534b is shaped enabling a snap type of assembly. It is understood that the second or upper disc replacement support truss pivot assembly formation 534b can be of any suitable size and shape that would enable a rotational assembly between the second or upper disc replacement support truss 510b and the proximal control arm rotational pivot shaft member 570. For example, the second or upper disc replacement support truss pivot assembly formation 534b can be a bore, a hole, a screwed on element, or any other suitable formation enabling a rotational motion between the second or upper disc replacement support truss 510b and the proximal control arm rotational pivot shaft member 570. In another arrangement, the second or upper disc replacement support truss 510b can include a pin, utilize a threaded element such as a screw or bolt, or any other arrangement enabling a rotational motion between the second or upper disc replacement support truss 510b and the proximal control arm rotational pivot shaft member 570.

The first or lower disc replacement support truss assembly and the second or upper disc replacement support truss assembly can utilize the same component; just oriented differently. Essentially, the first or lower disc replacement support truss assembly and the second or upper disc replacement support truss assembly are of the same size and shape.

In the exemplary surgically implantable spacer 500, an expansion and contraction drive subassembly (illustrated in FIG. 18) is employed to control an angle between the first or lower disc replacement support truss 510a and the second or upper disc replacement support truss 510b as well as the resulting distance between the distal end of the first or lower disc replacement support truss 510a and the distal end of the second or upper disc replacement support truss 510b. The expansion and contraction drive subassembly includes a proximal control arm rotational pivot shaft member 570 and a distal control arm rotational pivot shaft assembly 580 moveably assembled to one another by a threaded control member 590.

The proximal control arm rotational pivot shaft member 570 is similar to the proximal control arm rotational pivot shaft member 170 described above. Like elements of the proximal control arm rotational pivot shaft member 170 and the proximal control arm rotational pivot shaft member 570 are numbered the same, where the elements of the proximal control arm rotational pivot shaft member 570 are preceded by the numeral "5".

The threaded control member 590 is similar to the threaded control member 190 described above. Like elements of the threaded control member 190 and the threaded control member 590 are numbered the same, where the elements of the threaded control member 590 are preceded by the numeral "5".

In the exemplary surgically implantable spacer 500, the distal control arm rotational pivot shaft assembly 580 is of a different configuration compared to the distal control arm rotational pivot shaft member 180. The distal control arm rotational pivot shaft assembly 580 includes a threaded member receiving block 581 that is either assembled to a first distal control arm connecting element 583a and a second distal control arm connecting element 583b by any suitable assembly technique and/or components (as illustrated) or integral with the first distal control arm connecting element 583a and the second distal control arm connecting element 583b (as understood by description). The first distal control arm connecting element 583a and the second distal control arm connecting element 583b support a distal control arm rotational pivot shaft 588. It is understood that any suitable component can be utilized to connect the threaded member receiving block 581 and the distal control arm rotational pivot shaft 588 to one another. In one example, the first distal control arm connecting element 583a and the second distal control arm connecting element 583b can be provided as a single wishbone shaped component that is attached to one edge of the threaded member receiving block 581.

Operation of the expansion and contraction drive subassembly is similar to the system employed by the surgically implantable spacer 100 described above. As the threaded control member drive head 592 is rotated, the rotational motion is translated to a rotation of the threaded control member threaded shank 598 in either a clockwise or a counterclockwise direction. In one direction, the rotation draws the threaded member receiving block 581 towards a proximal control arm proximal end block 572 of the proximal control arm rotational pivot shaft member 570. In a second, opposite direction, the rotation draws the threaded member receiving block 581 away from the proximal control arm proximal end block 572 of the proximal control arm rotational pivot shaft member 570. The resulting motion is translated to a like motion of the distal control arm rotational pivot shaft 588.

A first or lower truss expansion control member 550a is pivotally assembled between the distal control arm rotational pivot shaft assembly 580 and the first or lower disc replacement support truss 510a. Similarly, a second or upper truss expansion control member 550b is pivotally assembled between the distal control arm rotational pivot shaft assembly 580 and the second or upper disc replacement support truss 510b. In the exemplary illustration, detailed in FIG. 19, a first or distal end of the first or lower truss expansion control member 550a is pivotally assembled to the distal control arm rotational pivot shaft 588 by a first or lower truss expansion control member pivot receiving feature 556a formed proximate the first or distal end of the first or lower truss expansion control member 550a. A second or proximal end of the first or lower truss expansion control member 550a is pivotally assembled to a first or lower disc replacement support truss spanning control cross member 516a by a first or lower truss expansion control member spanning control cross member receiving feature 554a formed proximate the second or proximal end of the first or lower truss expansion control member 550a. Similarly, a first or distal end of the second or upper truss expansion control member 550b is pivotally assembled to the distal control arm rotational pivot shaft 588 by a second or upper truss expansion control member pivot receiving feature 556b formed proximate the first or distal end of the second or upper truss expansion control member 550b. A second or proximal end of the second or upper truss expansion control member 550b is pivotally assembled to a second or upper disc replacement support truss spanning control cross member 516b by a second or upper truss expansion control member spanning control cross member receiving feature 554b formed proximate the second or proximal end of the second or upper truss expansion control member 550b.

Figure 20:
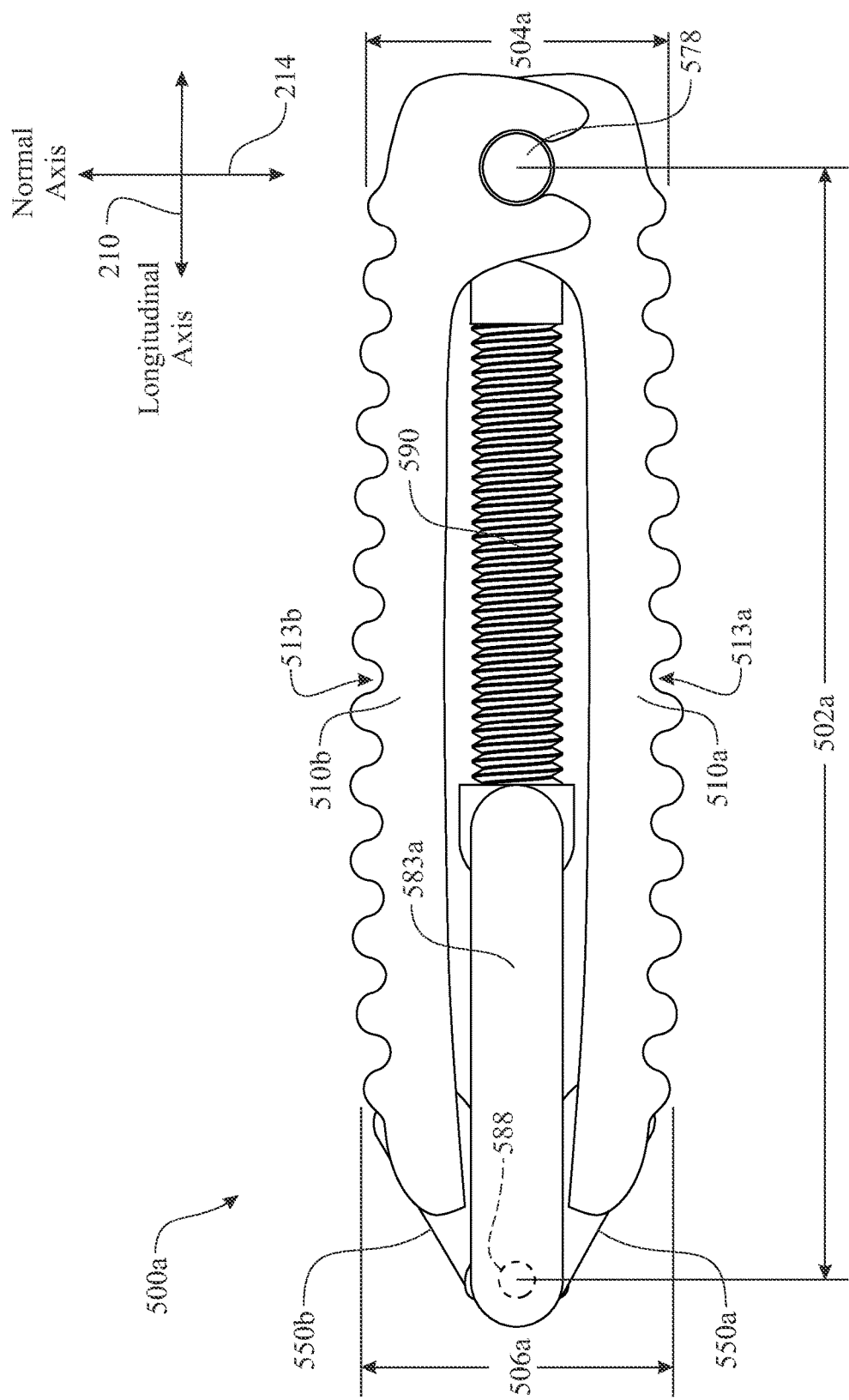
FIG. 20 presents a side elevation view of the exemplary surgically implantable spacer, originally introduced in FIG. 16, the surgically implantable spacer being shown in an initial vertebral contact configuration.
Figure 21:
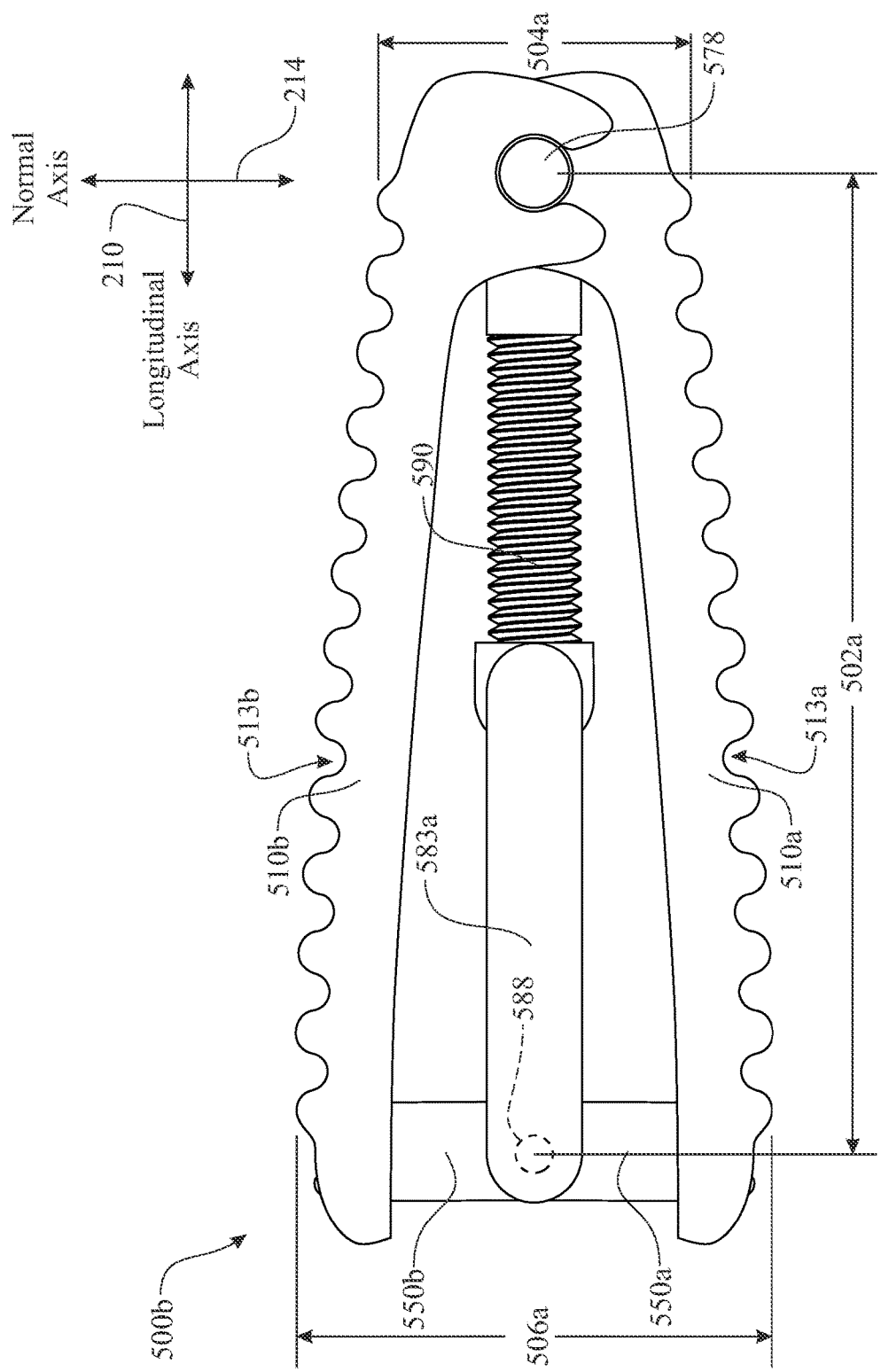
FIG. 21 presents a side elevation view of the exemplary surgically implantable spacer, originally introduced in FIG. 16, t the surgically implantable spacer being shown in a final installation configuration.

The surgically implantable spacer 500 is illustrated in a completely contracted or insertion configuration in FIG. 20 and the surgically implantable spacer 500 is illustrated in a completely expanded or installed configuration in FIG. 21.

As the expansion and contraction drive subassembly is expanded, the movement positions the 500 in the completely contracted or insertion configuration illustrated in FIG. 20.

An operational span dimension (installation configuration) 502a represents a farthest span between the proximal control arm rotational pivot shaft 578 and the distal control arm rotational pivot shaft 588. A distal end vertebral contacting span dimension (installation configuration) 506a represents a narrowest dimension between a first or lower disc replacement support truss joint contact surface 513a of the first or lower disc replacement support truss 510a at a distal end and a second or upper disc replacement support truss joint contact surface 513b of the second or upper disc replacement support truss 510b at a distal end. The distal control arm rotational pivot shaft assembly 580 is positioned towards the distal end, drawing the distal end of the first or lower truss expansion control member 550a and the distal end of the second or upper truss expansion control member 550b away from the proximal control arm rotational pivot shaft member 570. As a result, each of the first or lower truss expansion control member 550a and the second or upper truss expansion control member 550b rotate, bringing the proximal end of the first or lower truss expansion control member 550a and the proximal end of the second or upper truss expansion control member 550b towards the threaded control member 590. The rotational movement of the first or lower truss expansion control member 550a and the second or upper truss expansion control member 550b draws the distal end of the first or lower disc replacement support truss 510a and the distal end of the second or upper disc replacement support truss 510b towards the threaded control member 590.

The first or lower disc replacement support truss joint contact surface 513a and the second or upper disc replacement support truss joint contact surface 513b can comprise a retaining feature. Examples of retaining features include a series of ridges and recessions a9s shown), a textured surface, a series of spikes and valleys, and the like.

As the expansion and contraction drive subassembly is contracted, the movement positions the 500 in the completely expanded or installed configuration illustrated in FIG. 21. The distal control arm rotational pivot shaft assembly 580 is drawn towards the proximal control arm rotational pivot shaft member 570, drawing the distal end of the first or lower truss expansion control member 550a and the distal end of the second or upper truss expansion control member 550b towards from the proximal control arm rotational pivot shaft member 570. As a result, each of the first or lower truss expansion control member 550a and the second or upper truss expansion control member 550b rotate, driving the proximal end of the first or lower truss expansion control member 550a and the proximal end of the second or upper truss expansion control member 550b away from the threaded control member 590. The rotational movement of the first or lower truss expansion control member 550a and the second or upper truss expansion control member 550b separates the distal end of the first or lower disc replacement support truss 510a and the distal end of the second or upper disc replacement support truss 510b from the threaded control member 590.

An operational span dimension (maximum expansion configuration) 502b represents a narrowest span between the proximal control arm rotational pivot shaft 578 and the distal control arm rotational pivot shaft 588. A distal end vertebral contacting span dimension (maximum expansion configuration) 506b represents a farthest dimension between a first or lower disc replacement support truss joint contact surface 513a of the first or lower disc replacement support truss 510a at a distal end and a second or upper disc replacement support truss joint contact surface 513b of the second or upper disc replacement support truss 510b at a distal end. Since the first or lower disc replacement support truss 510a and the second or upper disc replacement support truss 510b rotation proximate the proximal end, a proximal end vertebral contacting span dimension (installation configuration) 504a and a proximal end vertebral contacting span dimension (maximum expansion configuration) 504b remain similar to one another.

The surgically implantable spacer 500 can be modified by introducing a second pair of truss expansion control members 550a, 550b on the proximal end. This arrangement would replicate the arrangement of the surgically implantable spacer 100 utilizing a majority of the elements of the surgically implantable spacer 500. The first or lower disc replacement support truss 510a and the second or upper disc replacement support truss 510b would be modified where the proximal end replicates the design of the distal end.

The surgically implantable spacer 100, 500 can be fabricated of any suitable material, using any suitable manufacturing process. The materials can include any material known and used for artificial discs. Examples of suitable materials include:

Polyethylene, a nonmetallic polymer made up of long molecular chains that can effectively transfer loads and provide high impact strength to the artificial disc, Titanium, a strong and corrosion-resistant metal with good elastic properties that encourages the growth of bone on the disc, an important feature for long-term stability, Cobalt-chrome, a mixture of cobalt and chromium metals, forming an alloy of high strength and stiffness, while also being corrosion resistant, and Stainless steel, made by mixing iron and carbon produces strong discs, although its mechanical properties may be inferior to its metallic counterparts.

The surgically implantable spacer 100, 500 can be fabricated using a machining process, a forging process, a molding process, a three-dimensional printing process, and the like, or any combination thereof.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

REF NO. DESCRIPTION 100 surgically implantable spacer
100 surgically implantable spacer
100a surgically implantable spacer (installation configuration)
100b surgically implantable spacer (initial vertebral contact configuration)
100c surgically implantable spacer (initial joint resistance configuration)
100d surgically implantable spacer (final installation configuration)
100e surgically implantable spacer (maximum expansion configuration)
102a operational span dimension (installation configuration)
102b operational span dimension (initial vertebral contact configuration)
102c operational span dimension (initial joint resistance configuration)

102*d* operational span dimension (final installation configuration)
102*e* operational span dimension (maximum expansion configuration)
104*a* proximal end vertebral contacting span dimension (installation configuration)
104*b* proximal end vertebral contacting span dimension (initial vertebral contact configuration)
104*c* proximal end vertebral contacting span dimension (initial joint resistance configuration)
104*d* proximal end vertebral contacting span dimension (final installation configuration)
104*e* proximal end vertebral contacting span dimension (maximum expansion configuration)
106*a* distal end vertebral contacting span dimension (installation configuration)
106*b* distal end vertebral contacting span dimension (initial vertebral contact configuration)
106*c* distal end vertebral contacting span dimension (initial joint resistance configuration)
106*d* distal end vertebral contacting span dimension (final installation configuration)
106*e* distal end vertebral contacting span dimension (maximum expansion configuration)
110*a* lower central disc replacement saddle member
110*b* upper central disc replacement saddle member
112*a* lower central disc replacement saddle body
112*b* upper central disc replacement saddle body
113*a* lower central disc replacement saddle body joint contact surface
113*b* upper central disc replacement saddle body joint contact surface
114*a* lower central disc replacement saddle first proximal hinge connecting formation
114*b* upper central disc replacement saddle first proximal hinge connecting formation
115*a* lower central disc replacement saddle second proximal hinge connecting formation
115*b* upper central disc replacement saddle second proximal hinge connecting formation
116*a* lower central disc replacement saddle first distal hinge connecting formation
116*b* upper central disc replacement saddle first distal hinge connecting formation
117*a* lower central disc replacement saddle second distal hinge connecting formation
117*b* upper central disc replacement saddle second distal hinge connecting formation
118*a* lower central disc replacement saddle hinge connecting formation interlocking gap
118*b* upper central disc replacement saddle hinge connecting formation interlocking gap
120*a* lower central disc replacement saddle contraction element clearance
120*b* upper central disc replacement saddle contraction element clearance
122*a* lower central disc replacement saddle body central clearance
122*b* upper central disc replacement saddle body central clearance
130*a* lower proximal expansion control arm member
130*b* upper proximal expansion control arm member
132*a* lower proximal expansion control arm section
132*b* upper proximal expansion control arm section
134*a* lower proximal expansion control arm first central hinge connecting formation
134*b* upper proximal expansion control arm first central hinge connecting formation
135*a* lower proximal expansion control arm second central hinge connecting formation
135*b* upper proximal expansion control arm second central hinge connecting formation
136*a* lower proximal expansion control arm first proximal hinge connecting formation
136*b* upper proximal expansion control arm first proximal hinge connecting formation
137*a* lower proximal expansion control arm second proximal hinge connecting formation
137*b* upper proximal expansion control arm second proximal hinge connecting formation
138*a* lower proximal expansion control arm hinge connecting formation interlocking gap
138*b* upper proximal expansion control arm hinge connecting formation interlocking gap
140*a* lower proximal expansion control arm bridge segment
140*b* upper proximal expansion control arm bridge segment
142*a* lower proximal expansion control arm contraction element clearance
142*b* upper proximal expansion control arm contraction element clearance
144*a* lower proximal expansion control arm transverse assembly retention element
144*b* upper proximal expansion control arm transverse assembly retention element
150*a* lower distal expansion control arm member
150*b* upper distal expansion control arm member
152*a* lower distal expansion control arm section
152*b* upper distal expansion control arm section
154*a* lower distal expansion control arm first central hinge connecting formation
154*b* upper distal expansion control arm first central hinge connecting formation
155*a* lower distal expansion control arm second central hinge connecting formation
155*b* upper distal expansion control arm second central hinge connecting formation
156*a* lower distal expansion control arm first distal hinge connecting formation
156*b* upper distal expansion control arm first distal hinge connecting formation
157*a* lower distal expansion control arm second distal hinge connecting formation
157*b* upper distal expansion control arm second distal hinge connecting formation
158*a* lower distal expansion control arm hinge connecting formation interlocking gap
158*b* upper distal expansion control arm hinge connecting formation interlocking gap
160*a* lower distal expansion control arm bridge segment
160*b* upper distal expansion control arm bridge segment
162*a* lower distal expansion control arm contraction element clearance
162*b* upper distal expansion control arm contraction element clearance
164*a* lower distal expansion control arm transverse assembly retention element
164*b* upper distal expansion control arm transverse assembly retention element
170 proximal control arm rotational pivot shaft member
172 proximal control arm proximal end block
174 proximal control arm smooth walled bore
176 proximal control arm contraction element seating flange
178 proximal control arm rotational pivot shaft 180 distal control arm rotational pivot shaft member
181 threaded member receiving block
182 distal control arm distal end block
183 distal control arm connecting shaft
184 threaded bore
185 installation aiding groove
188 distal control arm rotational pivot shaft
190 threaded control member
192 threaded control member drive head
194 threaded control member seating flange
196 threaded control member smooth shank
198 threaded control member threaded shank
210 longitudinal axis
212 lateral axis
214 normal axis
220 threaded control member rotational motion
222d distal rotational pivot shaft contraction motion
222p proximal rotational pivot shaft contraction motion
224a lower central disc replacement saddle member expansion motion
224b upper central disc replacement saddle member expansion motion
226a lower central disc replacement saddle member expansion resistance force
226b upper central disc replacement saddle member expansion resistance force
300 first joint member
302 first vertebrae
304 first vertebrae first joint surface
306 first vertebrae second joint surface
310 second joint member
312 second vertebrae
314 second vertebrae first joint surface
316 second vertebrae second joint surface
320 intra-vertebral disc
400 surgically implantable spacer insertion flow diagram
402 obtain correct surgically implantable spacer step
410 configuring surgically implantable spacer for insertion step
412 preparing joining for insertion of surgically implantable spacer step
420 insert surgically implantable spacer into joint step
422 contract elongated span of surgically implantable spacer step
424 expand span between joint contacting surfaces of the surgically implantable spacer step
426 initiate angular expansion between joint contacting surfaces of the surgically implantable spacer upon initial contact between the spacer and the joint surfaces step
428 terminate expansion between joint contacting surfaces of the surgically implantable spacer upon flush contact between the spacer and the joint surfaces step
430 introduce bone graft material optional step
500 surgically implantable spacer
502a operational span dimension (installation configuration)
502b operational span dimension (maximum expansion configuration)
504a proximal end vertebral contacting span dimension (installation configuration)
504b proximal end vertebral contacting span dimension (maximum expansion configuration)
506a distal end vertebral contacting span dimension (installation configuration)
506b distal end vertebral contacting span dimension (maximum expansion configuration)
510a first or lower disc replacement support truss
510b second or upper disc replacement support truss
513a first or lower disc replacement support truss joint contact surface
513b second or upper disc replacement support truss joint contact surface
516a first or lower disc replacement support truss spanning control cross member
516b second or upper disc replacement support truss spanning control cross member
534a first or lower disc replacement saddle member pivot assembly formation
534b second or upper disc replacement support truss pivot assembly formation
550a first or lower truss expansion control member
550b second or upper truss expansion control member
554a first or lower truss expansion control member spanning control cross member receiving feature
554b second or upper truss expansion control member spanning control cross member receiving feature
556a first or lower truss expansion control member pivot receiving feature
556b second or upper truss expansion control member pivot receiving feature
570 proximal control arm rotational pivot shaft member
572 proximal control arm proximal end block
574 proximal control arm smooth walled bore
578 proximal control arm rotational pivot shaft
580 distal control arm rotational pivot shaft assembly
581 threaded member receiving block
583a first distal control arm connecting element
583b second distal control arm connecting element
584 threaded bore
587 threaded member receiving block to connecting element assembly member
588 distal control arm rotational pivot shaft
590 threaded control member
592 threaded control member drive head
594 threaded control member seating flange
596 threaded control member smooth shank
598 threaded control member threaded shank
d distal end
p proximal end
Δ dimension difference

What is claimed is:

1. A surgically implantable spacer comprising:
a lower central disc replacement saddle member;
an upper central disc replacement saddle member;
a lower proximal expansion control arm member;
an upper proximal expansion control arm member;
a lower distal expansion control arm member;
an upper distal expansion control arm member;
a proximal control arm rotational pivot shaft member;
a distal control arm rotational pivot shaft member; and
a threaded control member,
wherein the lower central disc replacement saddle member and the lower proximal expansion control arm member are hingeably assembled at a proximal end of the lower central disc replacement saddle member, defining a lower proximal hinge,
wherein the lower central disc replacement saddle member and the lower distal expansion control arm member are hingeably assembled at a distal end of the lower central disc replacement saddle member, defining a lower distal hinge,
wherein the upper central disc replacement saddle member and the upper proximal expansion control arm member are hingeably assembled at a proximal end of the upper central disc replacement saddle member, defining an upper proximal hinge, wherein the upper central disc replacement saddle member and the upper distal expansion control arm member are hingeably assembled at a distal end of the upper central disc replacement saddle member, defining an upper distal hinge, wherein the lower proximal expansion control arm member and the upper proximal expansion control arm member are hingeably assembled to pivot about a proximal end of the surgically implantable spacer, defining a control arm member proximal hinge, wherein the lower distal expansion control arm member and the upper distal expansion control arm member are hingeably assembled to pivot about a distal end of the surgically implantable spacer, defining a control arm member distal hinge, wherein the threaded control member is arranged to draw the proximal end of the surgically implantable spacer and the distal end of the surgically implantable spacer towards one another causing the lower central disc replacement saddle member and the upper central disc replacement saddle member to separate from one another, wherein the lower proximal hinge and the lower distal hinge are spaced apart and arranged opposite each other at the proximal and distal ends, respectively, of the lower central disc replacement saddle member, wherein the upper proximal hinge and the upper distal hinge are spaced apart and arranged opposite each other at the proximal and distal ends, respectively, of the upper central disc replacement saddle member.

2. The surgically implantable spacer as recited in claim 1, the lower central disc replacement saddle member and the upper central disc replacement saddle member each further comprising a textured joint contact surface.

3. The surgically implantable spacer as recited in claim 1, at least one of the lower central disc replacement saddle member and the upper central disc replacement saddle member further comprising a central disc replacement saddle body central clearance.

4. The surgically implantable spacer as recited in claim 1, the threaded control member further comprising a threaded control member smooth shank section and a threaded control member threaded shank section.

5. The surgically implantable spacer as recited in claim 1, the threaded control member further comprising a threaded control member threaded shank section, wherein the threaded control member threaded shank section threadably engages with a threaded bore of a threaded member receiving block, the threaded member receiving block arranged to draw the proximal end of the surgically implantable spacer and the distal end of the surgically implantable spacer towards one another causing the lower central disc replacement saddle member and the upper central disc replacement saddle member to separate from one another.

6. The surgically implantable spacer as recited in claim 1, further comprising features on two different elements of the surgically implantable spacer that are pivotally connected to one another creating an interlaced arrangement between one another, wherein the interlaced arrangement retains the two different elements of the surgically implantable spacer in an assembled configuration, wherein the two different elements are selected from a group of elements consisting of:
the lower central disc replacement saddle member,
the upper central disc replacement saddle member,
the lower proximal expansion control arm member,
the upper proximal expansion control arm member,
the lower distal expansion control arm member, and
the upper distal expansion control arm member.

7. The surgically implantable spacer as recited in claim 1, wherein:
an axial length of the lower proximal expansion control arm member and an axial length of the upper proximal expansion control arm member are substantially similar;
an axial length of the lower distal expansion control arm member and an axial length of the upper distal expansion control arm member are substantially similar; and
the axial length of the lower proximal expansion control arm member and the axial length of the lower distal expansion control arm member are different from one another.

8. The surgically implantable spacer as recited in claim 1, wherein:
an axial length of the lower proximal expansion control arm member and an axial length of the upper proximal expansion control arm member are substantially similar;
an axial length of the lower distal expansion control arm member and an axial length of the upper distal expansion control arm member are substantially similar; and
the axial length of the lower proximal expansion control arm member is shorter than the axial length of the lower distal expansion control arm member.

9. The surgically implantable spacer as recited in claim 1, the threaded control member threadably assembled with a mating threaded element, wherein the threaded assembly between the control member threadable and the mating threaded element is located between the lower central disc replacement saddle member and the upper central disc replacement saddle member.

10. The method of implanting a surgically implantable spacer, the method comprising steps of:
obtaining a surgically implantable spacer;
expanding a span or distance between a proximal end of the surgically implantable spacer and a distal end of the surgically implantable spacer, minimizing a distance between a lower contacting surface of the surgically implantable spacer and an upper contacting surface of the surgically implantable spacer;
inserting the surgically implantable spacer into a biological joint;
contracting a distance between the proximal end of the surgically implantable spacer and the distal end of the surgically implantable spacer, increasing the distance between the lower contacting surface of the surgically implantable spacer and the upper contacting surface of the surgically implantable spacer,
wherein the lower contacting surface of the surgically implantable spacer and the upper contacting surface of the surgically implantable spacer move outward from one another in a parallel motion until a resistance force at a first end of the lower contacting surface of the surgically implantable spacer and a same first end of the upper contacting surface of the surgically implantable spacer is greater than a resistance force at a second, opposite end of the lower contacting surface of the surgically implantable spacer and a same second, opposite end of the upper contacting surface of the surgically implantable spacer such that a distance between the first ends of the lower contacting surface and the upper contacting surface and a distance between the second, opposite ends of the lower contacting surface and the upper contacting surface can vary respective to one another, wherein, upon the increase of the resistance force at the first end, the first end of the lower contacting surface of the surgically implantable spacer and the same first end of the upper contacting surface of the surgically implantable spacer expand at a reduced rate while a second, opposite end of the lower contacting surface of the surgically implantable spacer and a same second, opposite end of the upper contacting surface of the surgically implantable spacer continue to separate from one another at an original rate until a resistance force applied at the second, opposite end of the lower contacting surface of the surgically implantable spacer and the same second, opposite end of the upper contacting surface of the surgically implantable spacer equals the resistance force applied at the first end.

11. The method of implanting a surgically implantable spacer as recited in claim 10, the method further comprising a step of:

contracting a distance between the proximal end of the surgically implantable spacer and the distal end of the surgically implantable spacer by rotating a threaded control member.

12. The method of implanting a surgically implantable spacer as recited in claim 10, the method further comprising a step of:

positioning the lower contacting surface of the surgically implantable spacer and the upper contacting surface of the surgically implantable spacer in a non-parallel arrangement.

13. The method of implanting a surgically implantable spacer as recited in claim 10, the lower contacting surface of the surgically implantable spacer having an outwardly arched surface and the upper contacting surface of the surgically implantable spacer having an outwardly arched surface, the method further comprising steps of:

seating the outwardly arched surface of the lower contacting surface of the surgically implantable spacer against a first surface of the joint; and seating the outwardly arched surface of the upper contacting surface of the surgically implantable spacer against a second surface of the joint.

14. The method of implanting a surgically implantable spacer as recited in claim 10, the lower contacting surface of the surgically implantable spacer having a textured surface and the upper contacting surface of the surgically implantable spacer having a textured surface, the method further comprising steps of:

seating the textured surface of the lower contacting surface of the surgically implantable spacer against a first surface of the joint; and seating the textured surface of the upper contacting surface of the surgically implantable spacer against a second surface of the joint.

15. The method of implanting a surgically implantable spacer as recited in claim 10, further comprising a step of:

introduce bone graft material within an interior of the surgically implantable spacer.

16. A surgically implantable spacer comprising:

a proximal control arm rotational pivot shaft member comprising a proximal control arm proximal end block, a pair of proximal control arm rotational pivot shafts, each proximal control arm rotational pivot shaft extending linearly outward from opposite sides of the proximal control arm proximal end block, a proximal control arm smooth walled bore extending through the proximal control arm proximal end block in a direction generally perpendicular to an axial direction of the pair of proximal control arm rotational pivot shafts;

a distal control arm rotational pivot shaft assembly comprising a distal control arm rotational pivot shaft assembled to a threaded member receiving block by an assembly component, a threaded bore extending through the threaded member receiving block in a direction generally perpendicular to an elongated axis of the distal control arm rotational pivot shaft;

a threaded control member extending through the proximal control arm smooth walled bore and threadably assembled to the threaded bore extending through the threaded member receiving block;

a lower disc replacement support truss assembly comprising a near or first side lower disc replacement support truss, a far or second side lower disc replacement support truss and a lower spanning control cross member spanning between distal ends of the near or first side lower disc replacement support truss and the far or second side lower disc replacement support truss, each of the near or first side lower disc replacement support truss and the far or second side lower disc replacement support truss being pivotally assembled to the respective proximal control arm rotational pivot shaft of the pair of proximal control arm rotational pivot shafts;

a upper disc replacement support truss assembly comprising a near or first side upper disc replacement support truss, a far or second side upper disc replacement support truss and a upper spanning control cross member spanning between distal ends of the near or first side upper disc replacement support truss and the far or second side upper disc replacement support truss, each of the near or first side upper disc replacement support truss and the far or second side upper disc replacement support truss being pivotally assembled to the respective proximal control arm rotational pivot shaft of the pair of proximal control arm rotational pivot shafts;

a lower truss expansion control member having a first end pivotally assembled to the distal control arm rotational pivot shaft and a second, opposite end pivotally assembled to the lower disc replacement support truss spanning control cross member; and a upper truss expansion control member having a first end pivotally assembled to the distal control arm rotational pivot shaft and a second, opposite end pivotally assembled to the upper disc replacement support truss spanning control cross member.

17. The surgically implantable spacer as recited in claim 16, wherein the lower disc replacement support truss and the upper disc replacement support truss replicate one another in shape and size.

18. The surgically implantable spacer as recited in claim 16, wherein the lower truss expansion control member and the upper truss expansion control member replicate one another in shape and size.

19. The surgically implantable spacer as recited in claim 16, the lower disc replacement support truss further comprising a textured contacting surface and the upper disc replacement support truss further comprising a textured contacting surface.

20. The surgically implantable spacer as recited in claim 16, wherein the threaded assembly between the threaded control member and the threaded bore of the threaded member receiving block is located between the lower central disc replacement saddle member and the upper central disc replacement saddle member.

* * * * *